US006916424B2

(12) United States Patent
Collins et al.

(10) Patent No.: US 6,916,424 B2
(45) Date of Patent: Jul. 12, 2005

(54) METHOD AND APPARATUS FOR A HEMODIAFILTRATION DELIVERY MODULE

(75) Inventors: Gregory R Collins, Monroe, NY (US); James Summerton, Hillsdale, NJ (US); Edward Spence, Bronx, NY (US)

(73) Assignee: Nephros, Inc., New York, NY (US)

( * ) Notice: Subject to any disclaimer, the term of this patent is extended or adjusted under 35 U.S.C. 154(b) by 0 days.

(21) Appl. No.: 10/072,464

(22) Filed: Feb. 7, 2002

(65) Prior Publication Data

US 2002/0104800 A1 Aug. 8, 2002

Related U.S. Application Data

(60) Provisional application No. 60/267,103, filed on Feb. 7, 2001.

(51) Int. Cl.[7] .......................... B01D 61/28; B01D 61/24; B01D 61/32
(52) U.S. Cl. .................... 210/646; 210/645; 210/739; 210/929; 210/85; 210/86; 210/87; 210/88; 210/89; 210/90; 210/96.1; 210/96.2; 210/97; 210/98; 210/103; 210/104; 210/134; 210/136; 210/137; 210/138; 210/143; 210/252; 210/321.6; 210/321.72; 210/323.2; 604/4.01; 604/5.01
(58) Field of Search .............................. 210/85, 86, 87, 210/88, 89, 90, 96.1, 96.2, 97, 98, 103, 104, 134, 136, 137, 138, 143, 252, 321.6, 321.72, 323.2, 645, 646, 739, 929; 604/4.01, 5.01

(56) References Cited

U.S. PATENT DOCUMENTS

| 4,708,802 A | | 11/1987 | Rath et al. ................. 210/641 |
| 4,711,715 A | * | 12/1987 | Polaschegg ................ 210/103 |
| 4,993,269 A | * | 2/1991 | Guillaume et al. ....... 73/861.53 |
| 5,092,836 A | * | 3/1992 | Polaschegg ............... 604/6.11 |
| 6,039,877 A | * | 3/2000 | Chevallet et al. .......... 210/636 |
| 6,139,748 A | * | 10/2000 | Ericson et al. ............. 210/646 |
| 6,280,632 B1 | * | 8/2001 | Polaschegg ................ 210/739 |
| 6,284,141 B1 | * | 9/2001 | Shaldon et al. ............ 210/739 |
| 6,386,834 B1 | * | 5/2002 | Kimura et al. ........... 417/222.2 |
| 6,406,631 B1 | * | 6/2002 | Collins et al. ............. 210/646 |
| 6,423,231 B1 | * | 7/2002 | Collins et al. ............. 210/646 |
| 6,536,291 B1 | * | 3/2003 | Gysling et al. ............ 73/861.42 |
| 6,572,530 B1 | * | 6/2003 | Araki et al. ................ 600/17 |
| 6,691,584 B2 | * | 2/2004 | Gysling et al. ........... 73/861.42 |
| 2002/0023879 A1 | * | 2/2002 | Hadden ..................... 210/646 |

FOREIGN PATENT DOCUMENTS

| EP | 0516152 A1 | * 12/1992 | |
| WO | WO00/06292 | 2/2000 | ........... B01D/61/00 |

* cited by examiner

Primary Examiner—W. L. Walker
Assistant Examiner—K S Menon
(74) Attorney, Agent, or Firm—Darby & Darby

(57) ABSTRACT

This invention provides a method and apparatus for a hemodiafiltration delivery module that is used in conjunction with a UF controlled dialysis machine to enable hemodiafiltration therapy to be performed. The advantage is that one can fully utilize a current functioning dialysis machine to perform a hemodiafiltration therapy as opposed to purchasing a completely new machine that offers this capability.

41 Claims, 19 Drawing Sheets

METHOD AND APPARATUS FOR A HEMODIAFILTRATION DELIVERY MODULE

CROSS REFERENCE TO RELATED APPLICATION

This application claims the benefit of U.S. patent application serial No. 60/267,103, filed Feb. 7, 2001, and which is hereby incorporated by reference in its entirety.

FIELD OF THE INVENTION

The invention relates to blood cleansing systems in general and, more particularly, to a blood cleansing modality commonly referred to as hemodialysis and/or hemodiafiltration.

BACKGROUND OF THE INVENTION

Hemodiafiltration combines both standard hemodialysis and hemofiltration into one process, whereby a dialyzer cartridge containing a high flux membrane is used to remove substances from the blood both by diffusion and by convection. The removal of substances by diffusion is accomplished by establishing a concentration gradient across a semipermeable membrane by flowing a dialysate solution on one side of the membrane while simultaneously flowing blood on the opposite side of the membrane. In existing systems, to enhance removal of substances using hemodiafiltration, a solution called substitution fluid is continuously added to the blood either prior to the dialyzer cartridge (pre-dilution) or after the dialyzer cartridge (post-dilution). An amount of fluid equal to that of the added substitution fluid is ultrafiltered across the dialyzer cartridge membrane carrying with it additional solutes.

Substitution fluid is usually purchased as a sterile/non-pyrogenic fluid (eg. 0.9% saline solution or Ringer's Lactate solution) contained in large flexible bags. The disadvantage of using this type of fluid for hemodiafiltration is the relatively high cost associated with using large volumes during treatment. As a result, methods have been developed for producing substitution fluid on-line by filtration of a non-sterile dialysate through a suitable filter cartridge rendering it sterile and non-pyrogenic. Techniques for online production of substitution fluid have been described in the literature, for example, in B. Canaud, et al., "Hemodiafiltration Using Dialysate as Substitution Fluid", Artificial Organs, Vol. 12, No. 2 (1987), pp. 188–190. Here, a series of filter cartridges and a substitution pump were used in conjunction with a dialysis machine as a means to generate on-line substitution fluid for the purposes of performing hemodiafiltration. What is not described, however, is how the substitution pump is operated when the blood pump stops or when the dialysis machine goes into bypass which prevents dialysate being delivered to the dialyzer and substitution pump. It is understood by those skilled in the art, that a dialysis machine may suddenly stop the blood pump or go into a dialysate bypass mode in response to a machine alarm condition (eg. due to excessive extracorporeal circuit pressure or a low or high dialysate conductivity reading). When this happens, the substitution pump should immediately be disabled or turned OFF as a means to prevent a hazardous condition from occurring (eg. creating an excessive transmembrane pressure across the dialyzer membrane).

Dialysis machine manufacturers have developed standalone dialysis machines with on-line substitution fluid suitable for hemodiafiltration. One example is the Fresenius OnLine Plus™ System, available from Fresenius Medical Care of Bad Homburg, Germany. A second example, available from Gambro AB of Lund Sweden, has been described in the literature, for example, in D. Limido et al., "Clinical Evaluation of AK-100 ULTRA for Predilution HF with On-Line Prepared Bicarbonate Substitution Fluid. Comparison with HD and Acetate Postdilution HF", International Journal of Artificial Organs, Vol. 20, No. 3 (1997), pp. 153–157. In these systems, control of the substitution fluid pump by the dialysis machine is coordinated in such a manner as to prevent unsafe or hazardous conditions.

In general, dialysis machines are replaced every seven years on average and cost approximately $20,000. Currently there are about 45,000 dialysis machines being used around the world, with only a very small percentage of these machines being capable of performing hemodiafiltration with online substitution fluid. Because hemodiafiltration provides a better treatment over current hemodialysis, there exists a clear need for a clinical practitioner to offer this mode of renal replacement therapy to his/her patients. As an alternative to purchasing a new hemodiafiltration machine (eg. capable of producing online substitution fluid), the present applicants have developed a diafiltration delivery module that enables online hemodiafiltration to be performed safely with an existing ultrafiltration (UF) controlled dialysis machine.

SUMMARY

This invention provides a method and apparatus for a hemodiafiltration delivery module that is used in conjunction with a UF controlled dialysis machine to enable hemodiafiltration therapy to be performed. The advantage is that one can fully utilize a current functioning dialysis machine to perform a hemodiafiltration therapy as opposed to purchasing a completely new machine that offers this capability.

It is an object of the present invention to overcome safety issues that arise when there is no coordination between dialysis machine events (eg. alarm conditions, mode shifts, etc.) and an externally controlled substitution fluid pump. In particular, it an object of the invention to prevent unsafe or hazardous conditions, such as can occur when the substitution pump continues to pump fluid after the blood pump on the dialysis machine stops circulating blood through the extracorporeal circuit or after the dialysis machine stops delivering dialysate fluid to the substitution pump and dialyzer.

In addition, it is an object of the invention to prevent blood from contaminating the final sterilizing filter (referred to as a substitution fluid filter cartridge) and thus enable the sterilizing filter to be used multiple times without having to disinfect or replace the sterilizing filter between each treatment. It is also an object of the invention to be able to provide sterile substitution fluid that can be used for priming and blood rinseback as well as providing a fluid bolus to the patient during treatment. A further object of the invention is to provide a method and apparatus that can be rinsed and disinfected either in conjunction with the dialysis machine or independently from the dialysis machine. Additional objects of the invention are to provide a means to detect when the substitution filter becomes plugged, such as by measuring the filter water permeability, and provide a means to detect the integrity of the substitution filter(s) as well as the fluid path of the diafiltration module. And finally, it is an object of the invention to fully pass the dialysate stream through at least a first filtering stage of a substitution filter, thereby improving the quality of the dialysate introduced into the dialysate compartment of the dialyzer.

According to an aspect of the invention, the hemodiafiltration delivery module is used in conjunction with a dialysis machine that provides ultrafiltration (UF) control as is known in the art, for example the Fresenius 2008 series dialysis machine available from Fresenius Medical Care, Lexington, Mass., or Cobe CentrySystem 3 dialysis machine available from Cobe, Lakewood, Colo. In addition, a sterilizing filter cartridge containing at least one filtration stage is used to filter the non-sterile dialysate solution and thus render it sterile and non-pyrogenic. The sterilizing filter cartridge may contain a redundant filter stage as an added measure of safety, i.e. should one of the filters fail during the diafiltration treatment. The configuration is such that fresh dialysate from the dialysis machine passes through the diafiltration delivery module prior to being delivered to the dialyzer cartridge. A portion of this dialysate fluid is drawn off from the dialysate stream by the diafiltration delivery module and is passed through the sterilizing filter (or filters) by use of a substitution pump. The sterilizing filter cartridge effectively removes bacteria that may be present in the dialysate fluid. In addition, endotoxins and other particulate material are also effectively filtered out of the dialysate to make the dialysate fluid non-pyrogenic and of suitable injectable quality. The sterile filtered dialysate fluid is then introduced into the extracorporeal circuit as a substitution fluid for diafiltration via an infusion tubing segment connecting the outlet port of the final sterilizing filter and an inlet port of the extracorporeal circuit. Due to the UF control system (which includes dialysate flow balancing components), a substantially equal volume of plasma water will be filtered across the dialyzer membrane into the dialysate compartment to make up for the "missing" volume of dialysate fluid that is drawn off by the diafiltration delivery module. As indicated above, the dialysate fluid that is not used as substitution fluid is reintroduced into the dialysate compartment of the dialyzer. Generally speaking, the process of removing and filtering a portion of dialysate fluid for use as a sterile fluid that is infused into the extracorporeal circuit as a substitution fluid is known in the art as "online hemodiafiltration".

During normal operation of the invention when performing a diafiltration treatment, the diafiltration delivery module monitors at least two parameters to assure that the diafiltration process can be safely carried out. One parameter is associated with an adequate flow of dialysate through the diafiltration delivery module, such that sufficient substitution fluid can be generated. The other parameter is associated with an adequate flow of blood through the extracorporeal circuit. The latter is meant to assure that the blood does not become over hemoconcentrated as it passes through the dialyzer portion of the circuit. If this occurs, it can result in blood clotting in the dialyzer and a subsequent reduction of performance. In a first embodiment of the invention, flow meters are used to sense actual flow rates of each fluid stream (i.e. dialysate and blood flow rate). Outputs from these flow meters are used in a feedback control loop to control the substitution pump speed. In a second embodiment of the invention, a flow switch is used to detect for an adequate dialysate flow, while pressure pulses (caused by the inherent action of the peristaltic blood pump) are used as an indirect means to monitor blood flow rate. Pressure pulses are sensed either by a pressure transducer in fluid communication with one of the dialysis machine bloodline drip chamber pressure monitors or are sensed non-invasively by use of a strain gauge device that is placed in physical contact with a flexible portion of the bloodline circuit, preferably near the peristaltic blood pump. In a third embodiment, temperature sensors are used as an indirect measure of flow rate. Here, an indwelling temperature probe is placed directly in the dialysate fluid stream in the diafiltration delivery module while a surface temperature probe is placed in contact with the outside surface of the venous blood tubing line near dialyzer blood outlet. If blood flow through the extracorporeal circuit stops (eg. such as caused by a dialysis machine alarm condition), or if dialysate flow into the diafiltration delivery module becomes interrupted (eg. dialysis machine goes into a bypass mode), the extracorporeal blood and/or the dialysate fluid within the diafiltration module will begin to cool. When the rate of temperature decay exceeds a specified value, the substitution pump may be stopped to disable the diafiltration process. In a fourth embodiment, blood flow rate may be indirectly monitored using a tachometer that senses blood pump rotational speed. In a fifth embodiment, a photodiode array may be used to monitor drip chamber fluid level fluctuations (i.e. up and down motions of the fluid level within the drip chamber) caused by the peristaltic nature of the blood pump. In a sixth embodiment, dialysate flow may be indirectly monitored by inductively sensing the electrical current supplied to one of the dialysis machine solenoid valves that are associated with putting the machine in a bypass state. In addition, blood flow may be indirectly monitored by inductively sensing the electrical current supplied to the dialysis machine blood pump. In a seventh embodiment, blood flow rate may be indirectly monitored by sensing vibrations generated by the blood pump during treatment. These vibrations may be sensed mechanically using a vibration transducer that is in direct contact with a surface of dialysis machine, preferably near the blood pump, or sensed acoustically using a microphone or other sound detection device.

According to another aspect of the invention, the diafiltration delivery module prevents blood from backing up into the sterilizing filter. This has the advantage that the sterilizing filter can be used multiple times for subsequent treatments without having to discard and/or reprocess the sterilizing filter between treatments. In the first embodiment of the invention, this is accomplished by use of solenoid actuated pinch valve that is positioned on the flexible infusion tubing connected between the sterilizing filter and the extracorporeal filter. Control of the pinch valve is such that the valve is only opened when certain conditions are met, such as a minimum pre-filter pressure is achieved. The pinch valve may be automatically closed whenever an optical blood sensor (located between the pinch valve and the extracorporeal circuit) detects blood or when a sudden increase in pre-filter pressure is detected to be above a specified threshold value. In a seventh embodiment of the invention, a check valve is incorporated as part of the infusion tubing set as a secondary means to prevent blood from backing up into the sterilizing filter. This eliminates the need for the optical blood sensor described in the first embodiment. In an eighth embodiment of the invention, a peristaltic or roller (occluding type) pump is used in place of the pinch valve. This has the advantage of eliminating the need for the pinch valve and thus reducing the number of hardware components used in the diafiltration delivery module, however, this comes at the expense of requiring a special infusion line containing a pump segment that fits the substitution pump.

In a third aspect of the invention, it is desired to filter the entire dialysate stream as a means to improve the quality of dialysate entering the dialysate compartment of the dialyzer (in addition to generating sterile infusion fluid for diafiltration.) In an ninth embodiment of the invention, this is accomplished by running the substitution pump at a higher rate than the dialysate flow rate so that all the dialysate is filtered through at least a first filter stage of a sterilizing filter. A throttling valve placed in the fluid circuit on the downstream side of the first sterilizing filter is then used to generate a sufficient back pressure necessary to force the desired amount of substitution fluid through a second or final sterilizing filter. Adjustments to the aperture of the throttling valve may be based on input from a flow meter located on the dialysate stream leading to the dialyzer. As part of a tenth embodiment of the invention, it is also shown that one can control the rate of substitution fluid used for diafiltration using a feedback control loop based on flow restrictor devices and pressure inputs instead of the flow meter/throttling valve configuration. This has the distinct advantage in that one does not require use of an expensive flow meter and throttling valve to achieve this dialysate filtering aspect of the invention.

A fourth aspect of the invention includes being able to provide substitution fluid for other purposes besides diafiltration. For example, substitution fluid can be used for priming the extracorporeal circuit prior to treatment, for giving a fluid bolus during treatment, or for rinsing back the patient's blood at the end of treatment. In an embodiment of the invention, this may be accomplished by incorporation of an internal fluid reservoir as part of the diafiltration delivery module fluid path. Valves are appropriately included to enable one to switch flow from the incoming dialysate stream to the internal fluid reservoir as the source of substitution fluid for these purposes. This operation is necessary as the dialysis machine continuously balances fresh and spent dialysate fluid volumes as part of its UF control system. Filling of fluid reservoir is performed prior to therapy, such as part of a rinse or prime function.

Other aspects of the invention include a means to rinse and disinfect the diafiltration delivery module (with or without the sterilizing filter) as part of routine dialysis machine maintenance operations. Here, the diafiltration delivery module senses when there is an adequate flow of fluid (eg. rinse water) through the module as a means to assure fluid is available before turning on the substitution pump which circulates fluid through the module. Also, the dialfiltration delivery module can be configured as a standalone unit (with or without the sterilizing filter). In this mode, one can perform integrity tests on the fluid path and/or the sterilizing filter using the substitution pump to generate either positive or negative pressures in the fluid path circuit. Other tests, such as a filter plugging test, can be accomplished by recirculating fluid through the sterilizing filter at a known rate and measuring the ensuing pressure drop across the sterilizing filter. Also, by connecting an external reservoir (or reservoirs) containing a disinfecting solution and/or incorporating a heating module, disinfection of the dialfiltration module (with or without the sterilizing filter) may be accomplished in the standalone configuration.

And finally, in a tenth embodiment of the invention, it is further shown how the diafiltration delivery module may been separated into a treatment module and a reuse/test module. In this embodiment, the treatment module may be used without the reuse/test module when performing diafiltration treatments on the dialysis machine. In order to test the sterilizing filter and reprocess it for subsequent use, however, requires one to connect the reuse/test module to the treatment module to enable the test and disinfect functions to be performed. One advantage of this scheme is that the treatment module can be made much smaller as it contains only those components needed for carrying out the treatment aspects. This important because it is desirable to minimize the amount of space taken up by the diafiltration delivery module when connected to the dialysis machine. Another advantage has to do with preventing hazardous conditions associated with accidentally performing test/disinfect functions during treatment. For example, with separable modules, it would be impossible to invoke a hazardous disinfect process without the reuse/test module being connected to the treatment module.

DETAILED DESCRIPTION OF PREFERRED EMBODIMENTS

Figure 1A:
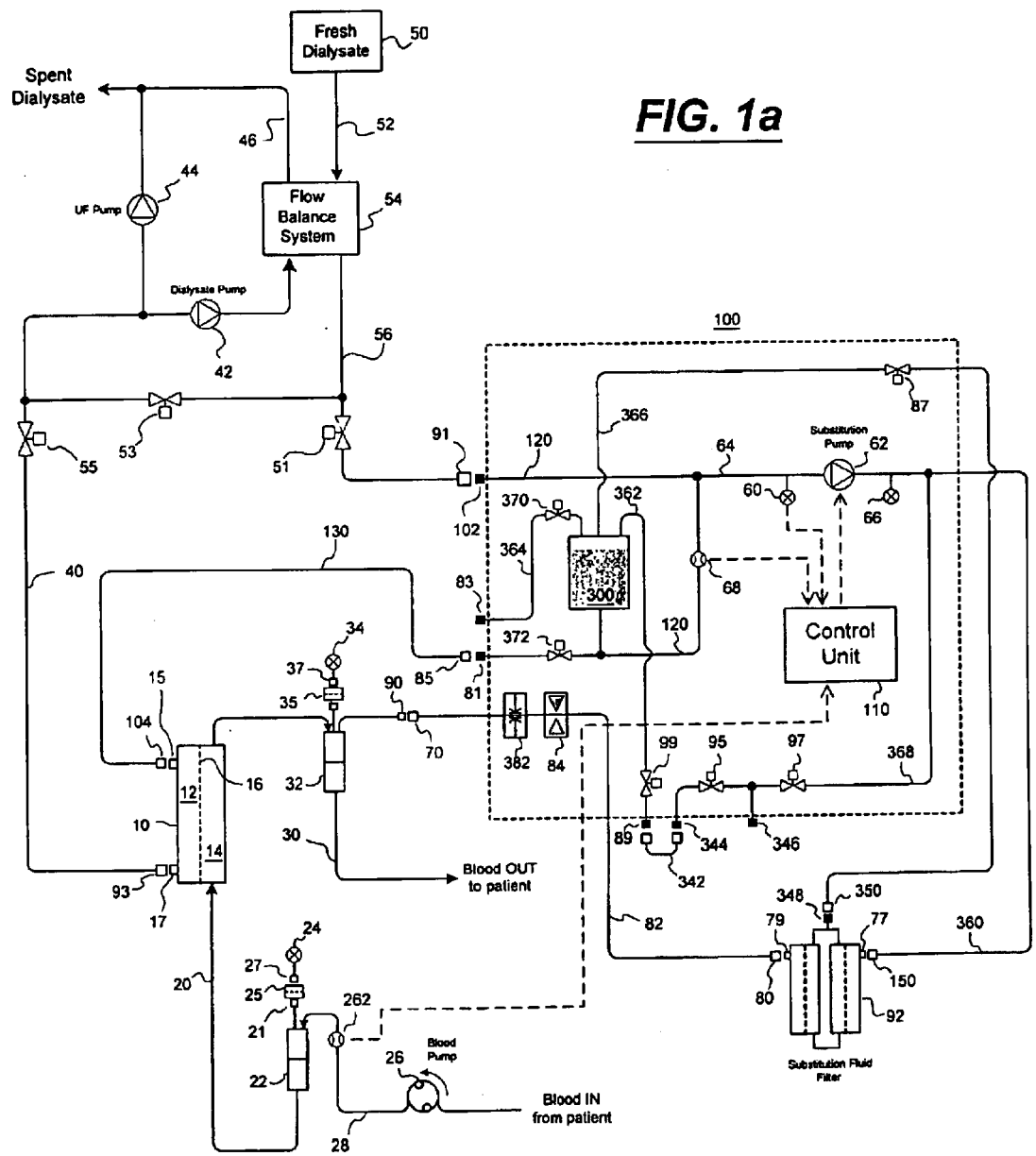
FIG. 1a is a schematic illustration of a diafiltration delivery module and sterilizing filter configured with a dialysis machine for diafiltration treatment in accordance with one embodiment.

In the embodiment of FIG. 1a, blood to be cleaned 20 is pumped by a blood pump 26 and enters a dialyzer cartridge 10. As shown in FIG. 1a, inlet blood circuit pressure may be measured upon exiting blood pump 26 by use of an arterial drip chamber 22 in the blood circuit between the pump 26 and the dialyzer cartridge 10. As known in the art, drip chamber pressure may be measured via a pressure monitoring line 21 that extends from the drip chamber 22. The monitoring line 21 is connected to a transducer protector 25 that is connected to a pressure monitoring port 27 on the dialysis machine. Connected to the pressure monitoring port 27 is a pressure transducer 24 that is used to measure the pressure in the drip chamber 22. The blood carrying tubing, known in the art as an arterial bloodline, may be made of a flexible polyvinylchloride (PVC) tubing. The blood flow rate is generally in the range of about 200 to about 700 ml/min, preferably 300 to 600 ml/min.

Dialyzer cartridge 10 contains a semi-permeable membrane 16 that divides the dialyzer cartridge 10 into a blood compartment 14 and a dialysate compartment 12. As blood passes through the blood compartment 14, plasma water containing blood substances may be filtered across the semi-permeable membrane 16. Additional blood substances are transferred across the semi-permeable membrane 16 by diffusion which is induced by a difference in concentration between the blood compartment 14 and the dialysate compartment 12. The dialyzer cartridge 10 used may be of any type suitable for hemodialysis, hemodiafiltration, hemofiltration, or hemoconcentration, as are known in the art. Preferably, the dialyzer cartridge 10 contains a medium or high flux membrane. Examples of suitable cartridges 10 include but are not limited to the Fresenius F60, Baxter CT 110, Hospal Filtral 16, or Minntech Hemocor HPH 1000.

Diafiltered blood exiting dialyzer cartridge 10 flows through a second blood carrying tubing, known in the art as a venous bloodline. The venous bloodline may use a drip chamber 32 as a means to measure blood circuit pressure downstream of the dialyzer cartridge 10. In a similar fashion to the arterial bloodline, pressure is measured via a monitoring line that is connected to a pressure transducer 35 that is connected to a pressure monitoring port 37. Connected to the pressure monitoring port 37 is a pressure transducer 34 that is used to measure the pressure in the venous drip chamber 32. As shown in FIG. 1a, substitution fluid that has been generated by a diafiltration delivery module 100 is introduced into the venous drip chamber 32 at connector 90 which is in fluid communication with conduit 82 via connector 70. This configuration is known in the art as a post-dilution diafiltration mode. It should be understood by those skilled in the art that the substitution fluid may be introduced into any suitable connection of the blood circuit. For example, it may be introduced into the arterial drip chamber 22 in a pre-dilution diafiltration mode, or if two dialyzers are used in series, it may be introduced in a mid-dilution mode (i.e. in a post-dilution mode relative to the first dialyzer and pre-dilution relative to the second dialyzer).

Fresh dialysate solution 50 prepared by the dialysis machine may be accomplished using any method known in the art, for example the volumetric proportioning method used in the Fresenius 2008 dialysis machine, available from Fresenius, Lexington, Mass., USA. Dialysate fluid is conveyed to a flow balancing system 54 via fluid path 52. The flow balancing system 54 may include any suitable devices known in the art, for example, volumetric balance chambers as used in the Fresenius 2008 dialysis machine, or dual flow meters as used in the Baxter 1550 dialysis machine, available from Baxter, Deerfield, Ill., USA. Fresh dialysate from the flow balance system 54 flows through a conduit 56 that leads to the diafiltration delivery module 100. Connection to the diafiltration delivery module 100 is accomplished by connecting the dialysis machine Hansen connector 91 to a suitable mating port 102 on the diafiltration delivery module 100. The fresh dialysate solution generally flows through a conduit 120 of the diafiltration delivery module 100 and exits the module via conduit 130 that connects to the inlet dialysate port 15 of the dialyzer cartridge 10 via connector 104. As will be described later, conduit 130 may be detachable from the diafiltration delivery module by use of a connector 85 and connector port 81. Spent dialysate exits the dialyzer cartridge 10 though a dialysate outlet port 17 and flows through a conduit 40 that is connected to the dialysate port 17 via a Hansen connector 93 as known in the art. The spent dialysate, which may be considered a mixture of dialysate, plasma water, and blood toxins that have crossed the semi-permeable membrane 16 of the dialyzer cartridge 10, is returned to the flow balancing system 54 via a dialysate pump 42. For ultrafiltration control purposes, a UF pump 44 may be used to bypass the flow balancing system as a means to remove a specified volume of fluid from the patient during the treatment. The dialysis machine generally includes a series of valves, such as indicated by valves 51, 53, and 55, that are used to shunt or divert dialysate away from the dialyzer. This is commonly known in the art as a "bypass mode" or a "cartridge isolate mode".

To generate sterile substitution fluid "online", a portion of the fresh dialysate fluid flowing through conduit 120 of the diafiltration delivery module 100 is drawn off by a substitution pump 62 via conduit 64. This portion of dialysate is pumped into conduit 360 that leads to the sterilizing filter 92 (indicated as "Substition Fluid Filter" in FIG. 1a). As shown, the substitution filter may include redundant sterilizing filters that are connected in a series arrangement as an extra safety precaution (i.e. should one of the filters fail during the treatment). The function of the substitution fluid filter 92 is to remove bacteria, endotoxins, and particulate from the dialysate fluid to render it suitable for injection into the blood circuit. After the dialysate fluid is passed through the substitution fluid filter 92, it flows through a flexible tubing conduit 82 that is connected to the blood circuit via connector 70. The flexible tubing 82 may be positioned in a solenoid actuated pinch valve 84 and an optical blood detector 382 which are used as a means to prevent the substitution fluid filter 92 from being contaminated by blood from the blood circuit. This will be described in further detail as part of the operational description of the invention.

Basic operation of the diafiltration delivery module during a diafiltration treatment is further described with reference to FIG. 1a and FIG. 1b which illustrate different control aspects of an embodiment of the invention. For example, FIG. 1a illustrates the feedback control mechanism used to control the substitution pump 62, whereas FIG. 1b illustrates the feedback control mechanism used to control the pinch valve 84.

In FIG. 1a, three inputs may be used as feedback control inputs to a control unit 110 that drives the speed of the substitution pump 62. These include a dialysate flow meter 68 that monitors dialysate flow rate through conduit 120, a blood flow meter 262 that monitors blood flow rate through the extracorporeal circuit, and a pre-substitution pump pressure transducer 60 that monitors inlet pressure of the substitution pump 62. The flow meter 68 may be of any type suitable for liquid flow, such as turbine flow meters, fixed volume metering chambers, mass flow meters, or thermal flow meters. In terms of the blood flow meter 262, this may be, but is not limited to, an ultrasonic flow meter device such as available from Transonic Systems, Ithica, N.Y., USA. In order for the substitution pump to be turned ON, at least two conditions must be met. First, an adequate dialysate flow rate must be sensed by the dialysate flow meter 68 and second, an adequate blood flow rate must be sensed by the blood flow meter 262. This assures that the machine is not in a bypass mode and that there is a sufficient amount of blood flowing through the dialyzer 10 to prevent over hemoconcentration during the diafiltration process. The third control input, dialysate pressure measured via pressure transducer 60, may be used as a back up control input to turn the substitution pump OFF when a specified negative pressure is detected. For example, if either of the flow meters 68, 262 failed during the treatment or the substitution pump ran at an excessive uncontrolled rate, a negative pressure would be detected by the pressure transducer 60. This would then be used to signal the control unit 110 to disable the substitution pump 62 and place the diafiltration delivery module in a safe state. It should be apparent to those skilled in the art that the invention thus prevents unsafe or hazardous conditions that can occur when the blood pump 26 on the dialysis machine stops circulating blood through the extracorporeal circuit or when the dialysis machine stops delivering dialysate fluid 50 to the dialyzer 10.

Figure 1B:
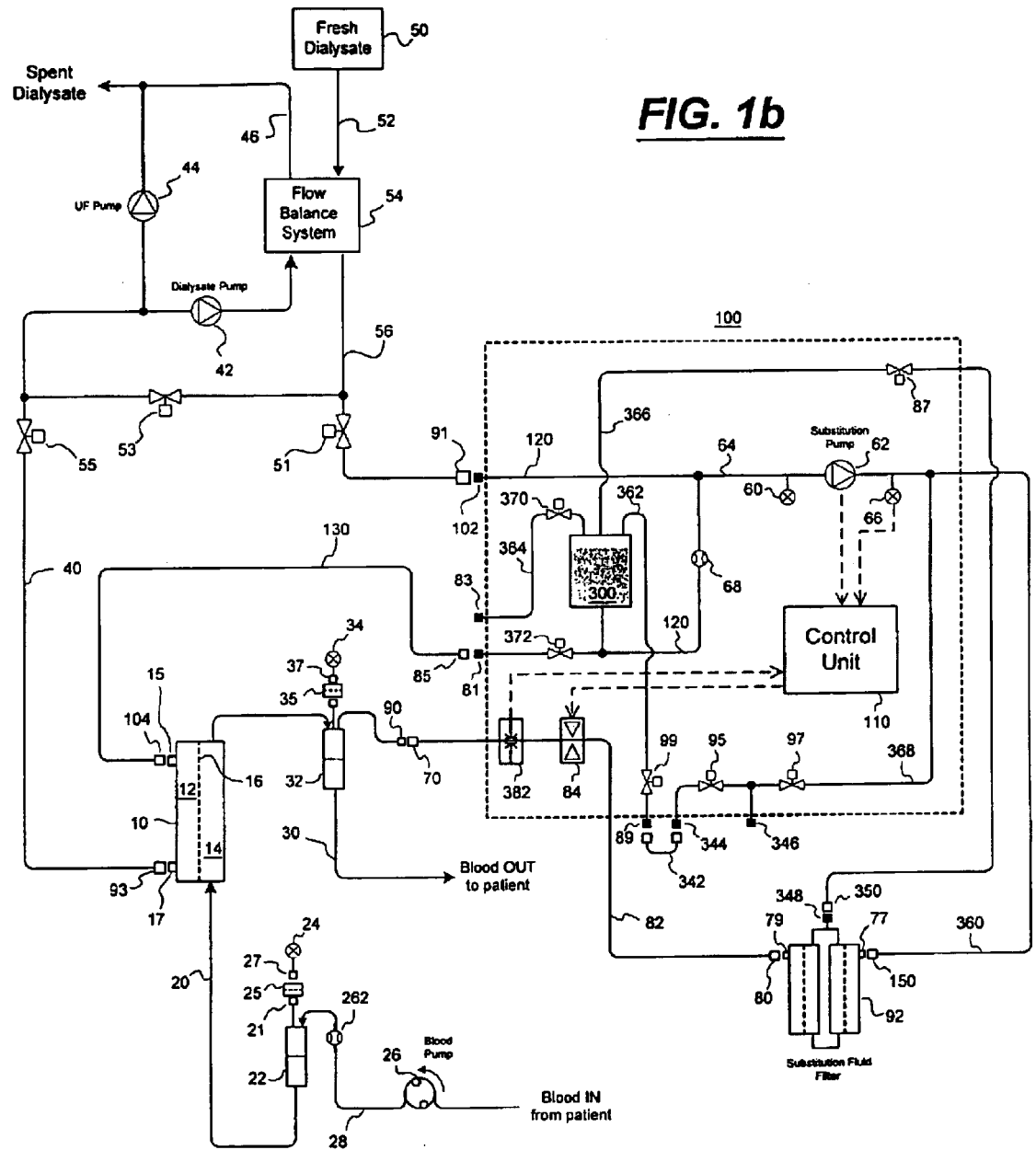
FIG. 1b is a schematic illustration of a diafiltration delivery module and sterilizing filter configured with a dialysis machine for diafiltration treatment in accordance with an embodiment of the invention depicting control of a pinch valve located on the infusion line between the sterilizing filter and the extracorporeal circuit.

In FIG. 1b, three inputs may be used as feedback control inputs to the control unit 110 that control the position of the pinch valve 84. These include a control signal from the substitution pump 62 to indicate it is ON and pumping, a pressure transducer 66 that monitors the downstream pressure of the substitution pump 62, and an optical blood sensor 382 that monitors the transmittance of the fluid contained in the substitution fluid tubing conduit 82. The optical sensor can be of any suitable type that includes a light source and a photo-detector combination to detect a loss of transmittance of light through the fluid contained in the tubing. In order for the pinch valve 84 to be opened, at least two conditions must be met. First, the substitution pump 62 must be turned ON and pumping dialysate fluid in the direction of the substitution fluid filter 92. Second, a minimum pressure sensed by pressure transducer 66 must be achieved that assures that substitution flow will remain in the forward direction into the extracorporeal circuit when the pinch valve 84 is opened. A third control input from the optical sensor 382 may be used as a back up control input to close the pinch valve 84 and place the diafiltration delivery module in a safe state whenever blood is detected in the substitution fluid tubing conduit 82. Here it should be apparent to those skilled in the art that the invention prevents blood from backing up into the substitution filter 92 and thus enabling the substitution filter 92 to be used multiple times for several treatments without the risk of cross contamination between patients. Again, we may want to refer to our other patent covering the valve mechanism for infusion fluid system.

Operation of the diafiltration delivery module 100 to deliver a fluid bolus during treatment is described as follows with reference back to FIG. 1a. In order to use the diafiltration delivery module 100 in a fluid bolus mode, the user will be instructed to place the dialysis machine in a bypass or cartridge isolate mode. This necessary to assure proper fluid balance is maintained during the course of giving the fluid bolus. Once the dialysis machine is placed in a bypass or cartridge isolate mode, such as achieved by closing valves 51 and 55 and opening valve 53, the dialysate flow through the diafiltration delivery module 100 will stop. Upon detecting there is no dialysate flow by flow meter 68, the diafiltration delivery module is automatically placed in a safe state (i.e. substitution pump 62 is turned OFF, pinch valve 84 is closed, and all valves including 372 is closed). Next, the substitution pump 62 is turned ON and thereafter valve 370 can be opened once a negative pressure is sensed at pressure transducer 60. The negative pressure condition assures fluid will not leak out of the module when valve 370 is opened to atmospheric pressure. As the substitution pump 62 continues to pump, air will enter through connector 81 and flow through conduit 364 leading to a fluid reservoir 300 that contains a source of dialysate fluid. The dialysate fluid from the reservoir 300 flows into conduit 120 and subsequently into conduit 64 leading to the substitution pump 62. On the discharge side of the substitution pump 62, pressure will increase since pinch valve 84 is in a closed posittition. Once a minimum pressure is achieved, the pinch valve 84 may be opened to allow substitution fluid to flow through conduit 82 and into the extracorporeal circuit. Provided the substitution pump 62 is a metering type pump, a specified volume of bolus fluid can be given based on pumping a certain number of strokes. If the substitution pump is not a metering type pump, it may be necessary for the user to monitor the amount of fluid given based on a visual observation of fluid level changes in the fluid reservoir 300. The means to provide substitution fluid for priming and rinseback are similar to that described above with the exception that the point of entry of substitution fluid into the extracorporeal circuit may be changed to a different location to achieve the best results.

Figure 1C:
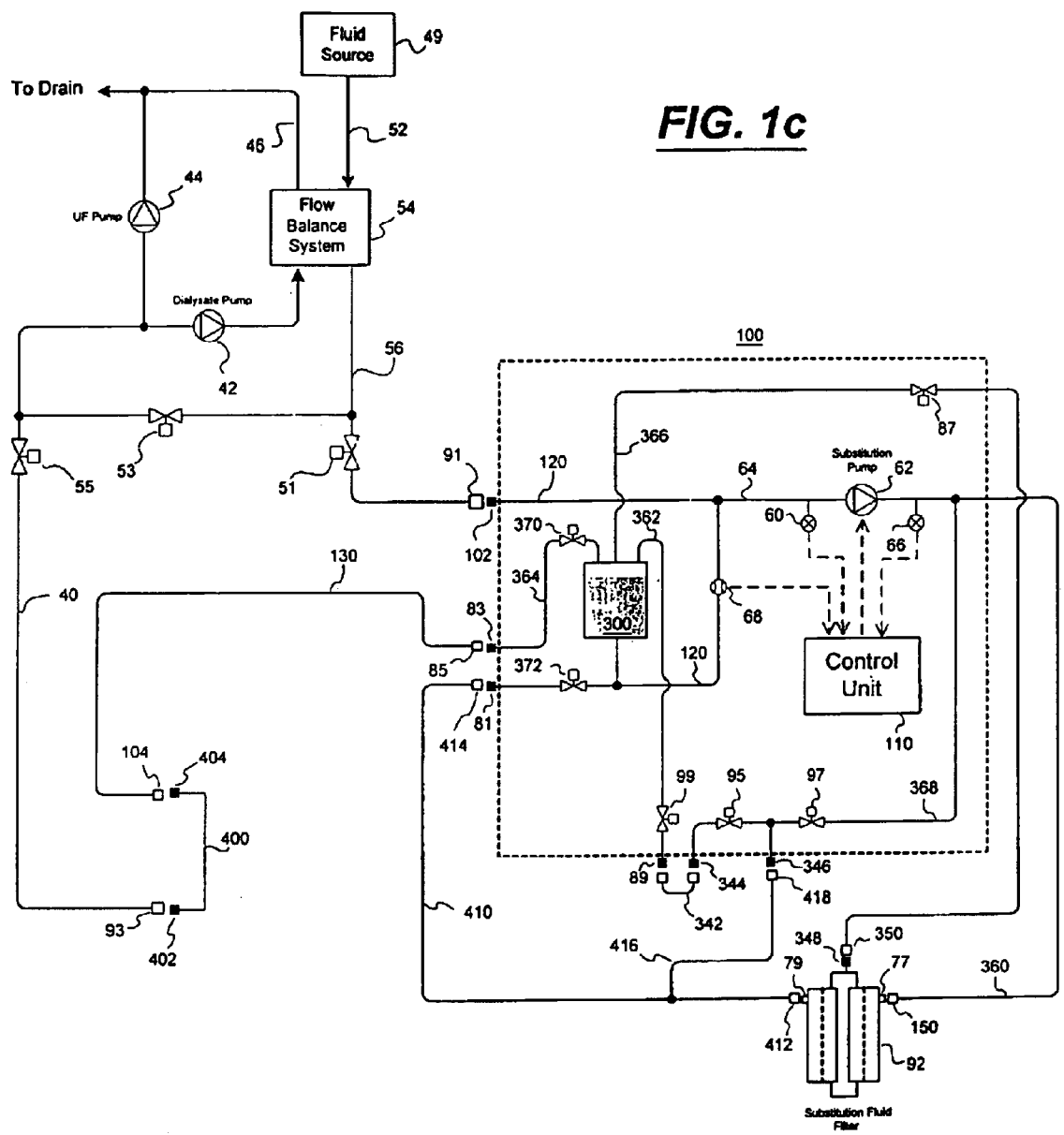
FIG. 1c is a schematic illustration of a diafiltration delivery module, sterilizing filter, and dialysis machine configured for rinsing or disinfection in accordance one embodiment.

Reference is now made to FIG. 1c which shows schematic illustration of a diafiltration delivery module 100 and the substitution filter 92 that has been configured for rinsing or disinfection in conjunction with the dialysis machine. Here the extracorporeal circuit and substitution fluid tubing conduit 82 have been removed and the associated dialysate female Hansen connectors 104 and 93 have been placed on their respective dialysis machine rinse ports 404 and 402 respectively. The dialysate conduit 130 with end connector 85 is placed on a mating rinse port 83. A substitution filter rinse line, which is made up of tubing conduits 410 and 416 connected in a tee configuration with associated end connectors 414, 418, and 412, is connected to rinse ports 81, 346, and substitution outlet port 79 respectively. Operation of the diafiltration delivery module during a machine rinse or disinfect cycle is as follows. The dialysis machine produces a source of fluid 49 that can be used for rinsing, disinfecting, or priming the fluid path of both the dialysis machine and the diafiltration delivery module 100. Fluid from the fluid source 49 is conveyed through conduit 52 to the flow balance system 54. From the flow balancing system 54, the fluid flows through conduit 56 and into the diafiltration delivery module 100 via connector 102. Generally, the fluid runs through the diafiltration delivery module 100 through conduit 120 and into the bottom of the fluid reservoir 300. The outlet of the reservoir 300 is located at the top so that air within the fluid reservoir 300 is effectively purged out through conduit 364 during the initial part of the cycle. Fluid exiting the diafiltration delivery module is returned to the dialysis machine through conduit 130 which is attached to the dialysis machine rinse block connector 404. In order to rinse or disinfect the remaining fluid path portions of the diafiltration delivery module 100 and substitution fluid filter 92, the dialysate flow meter 68 is monitored to ensure an adequate flow of fluid is passing through the module 100. When an adequate flow has been determined, the substitution pump 62 can be turned ON to initiate flow through conduit 64 and conduit 360 leading to the substitution fluid filter 92. By selectively opening and closing valves, it is possible to direct the fluid though select portions of the fluid path. For example, by closing valves 97, 95, 99, and 87 and opening valve 372, one can direct fluid across the substitution fluid filter 92 and through conduit 410 that leads back to the fluid reservoir 300. By closing valve 372 and opening valve 87, one can direct fluid through a first filter stage of the substitution fluid filter 92 and though a conduit 366 that leads back to the fluid reservoir 300. By closing valve 87 and opening valves 97 and 372, one can direct a portion of fluid from the substitution pump into conduit 368 and through conduit 416 that leads to conduit 410 in fluid communication with the fluid reservoir 300. By closing off valve 372 and opening valves 95 and 99, one can direct flow from conduit 368 into conduits 342 and 362 that is in fluid communication with the fluid reservoir 300. It should be apparent to those skilled in the art that the fluid path of the diafiltration delivery module 100 does not contain any dead legs and as such can be properly primed, rinsed, disinfected because one can expose the entire fluid path to dialysate for the purpose of priming, water for the purpose of rinsing, or a disinfectant solution for the purpose of disinfection.

Figure 1D:
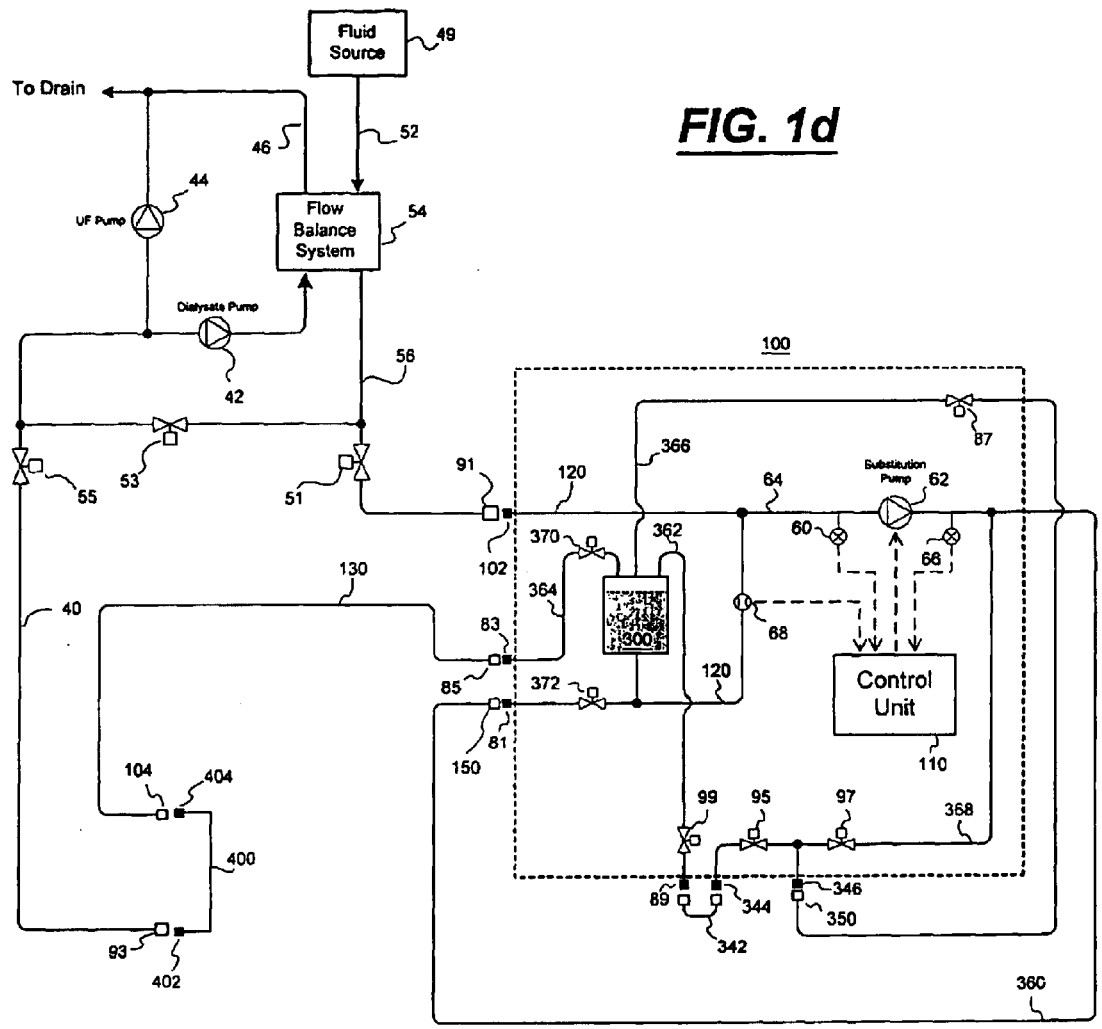
FIG. 1d is a schematic illustration of a diafiltration delivery module and dialysis machine configured for rinsing or disinfection without the sterilizing filter in accordance with one embodiment.
Figure 1D:
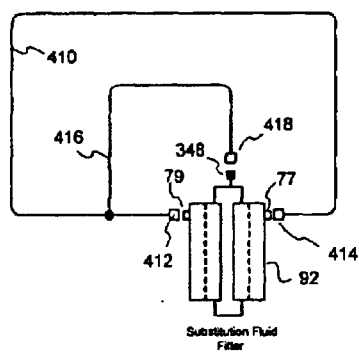

Reference is now made to FIG. 1d that illustrates the configuration when the substitution filter 92 and its associated rinse line has been separated from the diafiltration delivery module 100. Here, rinse line connectors 414 and 418 are detached from the diafiltration module while connectors 350 and 150 are detached from the substitution fluid filter. Connectors 150, 350, 414, 418 are then reconnected as follows. Connectors 414 and 418 are attached to the substitution filter ports 77 and 348 respectively. Connectors 150 and 350 are attached to the diafiltration delivery module ports 81 and 346 respectively. Operation of the diafiltration delivery module 100 in this configuration is similar to that described above with reference to FIG. 1c. For example, the dialysis machine produces a source of fluid 49 that can be used for rinsing, disinfecting, or priming the fluid path of both the dialysis machine and the diafiltration delivery module 100. Valves may then used to direct flow through different sections of the diafiltration delivery module fluid path as a means to fully expose the fluid path with the dialysis machine source fluid 49. Also, it should be apparent to those skilled in the art, that the rinse line (made up of conduits 410 and 416 and connectors 412, 414, and 418) helps contain fluid within the substitution fluid filter cartridge 92. This can be advantageous with respect to storage of the filter between uses, for example if it has been filled with a disinfectant solution that requires a dwell period as part of the disinfection procedure.

Figure 1E:
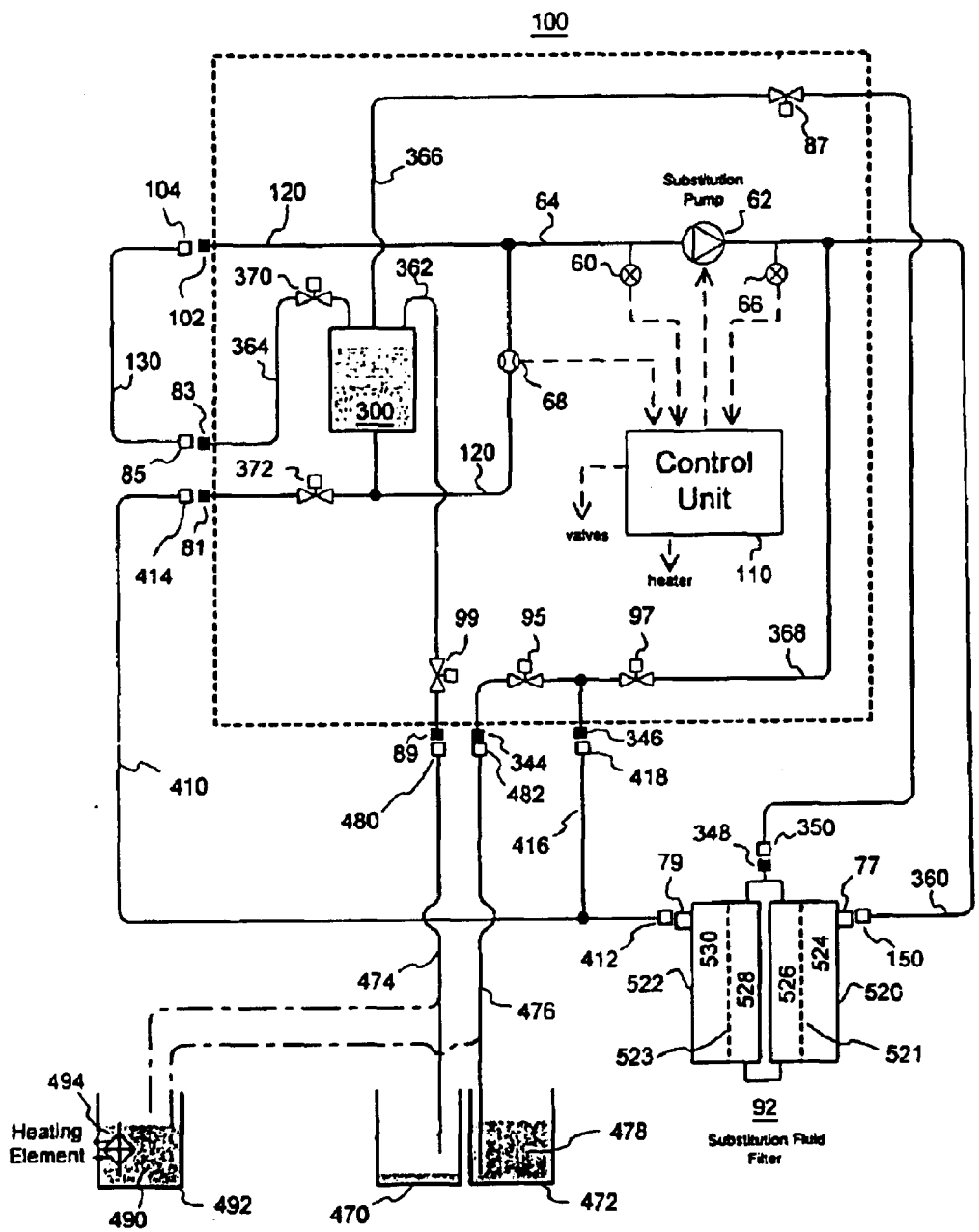
FIG. 1e is a schematic illustration of a diafiltration delivery module and sterilizing filter in a standalone configuration for testing and disinfection purposes in accordance with one embodiment.

Reference is now made to FIG. 1e showing a diafiltration delivery module and substitution fluid filter cartridge that has been configured in a standalone mode for testing and disinfection. The differences between this configuration and that shown in FIG. 1c is as follows. Dialysis machine connector 91 has been detached from the diafiltration delivery module inlet port 102. The diafiltration module connector 104 has been detached from the dialysis machine rinse block port 404 and is subsequently connected to the diafiltration module inlet port 102. A diafiltration module shunt connector, which is made up of conduit 342 with appropriate end connecors that attach to module disinfection ports 89 and 344, is removed and tubing conduits 474 and 476 with end connectors 480 and 482 are attached to the diafiltration module disinfection ports 89 and 344 respectively. These conduits lead to either a single reservoir 492 or two reservoirs 470 and 472 respectively. For the case of a single reservoir 492, this reservoir holds a disinfection solution 490 and may contain heating element 494 as a means to perform a heat disinfection step. For the case of the two reservoirs, reservoir 472 holds a disinfection solution, while reservoir 470 serves primarily as a fluid collection vessel. Operations for carrying out various tests and disinfection routines are described in the following paragraphs.

In the standalone configuration, the diafiltration delivery module 100 may perform a fluid path integrity test to verify that the fluid path and connections to the substitution filter are intact. This may be accomplished by closing valves 87, 95, 99, and 372, while opening valves 97 and 370. The substitution pump 62 may then be turned ON in the forward direction for a period of time or until a certain pressure is observed at the discharge pressure transducer 66. Here, a positive pressure generally develops in the substitution filter cartridge 92 while a negative pressure is generated in the fluid reservoir 300. At the end of the pressurizing period, the substitution pump 62 may be turned OFF and, after a specified stabilization period, the control unit 110 may monitor the rate of pressure decay over a set test period. Any fluid path leaks may then be detected when the measured pressure decay exceeds a pre-determined limit. Similarly, a second integrity test may be performed with the substitution pump 62 operated in reverse direction. Here, a positive pressure generally develops in the fluid reservoir 300, while a negative pressure is generated in the substitution filter cartridge 92.

Next, a water permeability test may be performed as a means to monitor the degree of plugging of the substitution fluid filter 92. This may be accomplished by running the substitution pump 62 in the forward direction at a specified rate with all valves closed except for valve 372. Fluid then runs from the substitution pump 62, through conduit 360, across the substitution filter 92, through conduit 410, into conduit 120, and finally through conduit 64 where it is returned to the substitution pump 62. By monitoring pressures at pressure transducers 60 and 66, one may determine the degree of plugging by comparing the resulting pressure differential relative to that of a new substitution filter.

A substitution filter membrane integrity test may also be performed. As shown in FIG. 1e, the substitution filter 92 may be comprised of a first sterile filter stage 520 and a second filter stage 522. The first filter stage 520 contains a semi-permeable membrane 521 that divides the first filter stage into a first upstream compartment 524 and a first downstream compartment 526, while the second filter stage 522 contains a semi-permeable membrane 523 that divides the second filter stage 522 into a second upstream compartment 528 and a second downstream compartment 530. The substitution filter 92 is configured such that is includes a port 348 that is in fluid communication with both the first downstream compartment 526 and the second upstream compartment 528. Membrane integrity testing of both filter stages may be accomplished simultaneously as follows. First, valves 372, 370, and 87 are closed while valves 99, 95, and 97 are opened. The substitution pump 62 is turned ON in the forward direction. A negative pressure ensues in fluid reservoir 300 that in turn draws air into conduit 474 and into conduit 362. Air enters the reservoir 300 and displaces the fluid initially contained in the reservoir such that it becomes partially full. The fluid from the reservoir 300 travels through conduit 120, into conduit 64, into parallel conduits 368 and 360. A portion of the fluid flows though conduit 360, across the substitution fluid filter 92 and into conduit 416. The other portion of fluid flows through conduit 368 and combines with the fluid from conduit 416. This fluid then flows through valve 95, into conduit 476 and finally into the fluid reservoir 472. After a specified amount of fluid has been pumped into the fluid reservoir 472 and before the fluid in reservoir 300 is emptied, the substitution pump is turned OFF. Next, valve 87 is opened and valve 95 is closed. The substitution pump 62 is turned on in the reverse direction such that a negative pressure is simultaneously generated at the inlet and outlet ports, 77 and 79, of the substitution filter 92. This will in turn draw fluid across both filter membranes 521 and 523 such that fluid flows from the first downstream compartment 526 into the first upstream compartment 524 and from the second upstream compartment 528 into the second downstream compartment 530. Because the first downstream compartment 526 and the second upstream compartment 528 are in fluid communication with the top of the fluid reservoir 300 via conduit 366, air in the top of the partially full fluid reservoir 300 will flow into conduit 366 and eventually into the filter compartments 526 and 528. When the fluid in compartments 526 and 528 is completely displaced by the air, the negative pressure as sensed by pressure transducer 66 should become more negative since air should not be able to cross the semi-permeable membranes 521 and 523, assuming they are intact. Upon reaching a specified negative pressure, the substitution pump 62 may be turned OFF provided it is an occluding type pump. After a specified stabilization period, the control unit 110 may monitor the rate of pressure decay over a set test period. Any substitution filter integrity leaks may then be detected when the measured pressure decay exceeds a predetermined limit as is known in the art as a pressure decay test. Upon passing the pressure decay test, refilling the substitution filter compartments 526 and 528 with fluid may be accomplished by turning on the substitution pump 62 in the forward direction such that fluid from the fluid reservoir 300 is drawn into conduit 120, into conduit 64, and through conduits 360 and 368 which lead to the substitution filter compartments 524 and 530. This will force fluid across the semi-permeable membranes 521 and 523 and into compartments 526 and 528 respectively, and thus push the air back into the fluid reservoir 300.

With continued reference to FIG. 1e, the diafiltration delivery module 100 with the accompanying substitution filter 92 may be loaded with a disinfectant solution for disinfection of the fluid path and substitution filter 92. For a chemical disinfection, a concentrated disinfecting solution 478 may be placed into the fluid reservoir 472. This fluid is drawn into the fluid path by opening valves 95, 97 and 99, closing valves 87, 370 and 372, and turning on the substitution pump 62 in the reverse direction with flow leading into conduit 64. Provided the substitution pump 62 is an occluding type pump, such as a metering pump, a specified volume of concentrated disinfecting solution 478 can be pumped into the fluid path. In addition, the fluid reservoir 300 may be filled by purging air out the top through conduit 362 that leads the fluid reservoir 470. Next, by opening and closing various valves in the fluid path, the concentrated disinfecting solution can be mixed with the fluid contained in the fluid path such that a uniform concentration can be achieved and such that all sections of the fluid path can be exposed to the resulting disinfecting solution. For example, with the substitution pump 62 turned ON in the forward direction, conduits 360, 410, 120, and 64 can be exposed with valve 372 opened and all others closed. Next, opening valve 97 additionally exposes conduit 416 to the disinfecting solution. By closing valves 372 and 97 and opening valve 87, conduits 360, 366, fluid reservoir 300, and conduits 120 and 64 may be exposed to the disinfecting solution. Next, opening valve 370 additionally exposes conduits 364, 130, and 120. As an alternative to a purely chemical disinfection process, one may configure conduits 474 and 476 such that they are both in fluid communication with a common fluid reservoir 492 which includes an electrical heating element 494. In this configuration, the fluid 490 contained in reservoir 492 may be pure water or may be a dilute citric acid/water solution (for example containing about 1% to 5% citric acid by weight). In a similar manner as above, by opening and closing various valves and by turning substitution pump 62 ON in the reverse direction, one may draw heated fluid from reservoir 492 into conduits 476 and 368 and pump this heated fluid through conduits 64 and 120 and into fluid reservoir 300. Next the heated fluid can be recirculated throughout the fluid path the same as described above. The main difference to the chemical disinfection process is that one may need to repeatedly draw heated fluid into the fluid path in order to maintain a minimum temperature during the heat disinfection process.

Figures 1F, 1G:
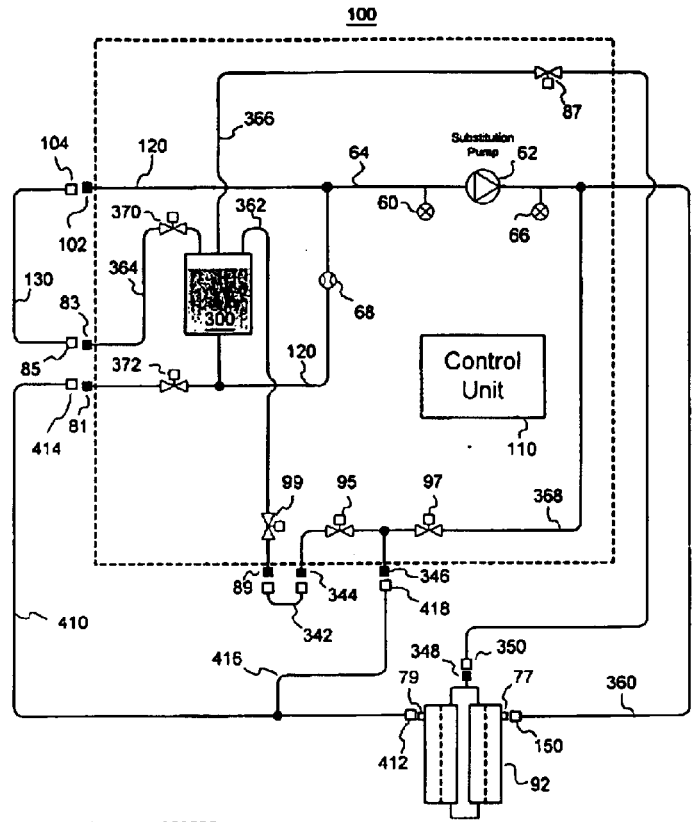
FIG. 1f is a schematic illustration of a diafiltration delivery module and sterilizing filter in a standalone configuration for disinfect dwell or storage purpose in accordance with one embodiment.
FIG. 1g is a schematic illustration of a diafiltration delivery module in a standalone configuration for disinfect dwell or storage purpose without a sterilizing filter in accordance with one embodiment.

Reference is now made to FIG. 1f that shows the diafiltration delivery module 100 with a substitution fluid filter 92 that has been configured in a self contained mode suitable for storage or chemical dwell periods as part of a fluid path disinfection process. This configuration is similar to that of FIG. 1e except conduits 474 and 476 have been removed from ports 89 and 344 respectively and replaced with the diafiltration module shunt connector containing conduit 342.

Reference is now made to FIG. 1g that shows the diafiltration delivery module 100 in a self contained mode after the substitution fluid filter 92 and its associated rinse line have been removed. This configuration is also suitable for storage or chemical dwell periods as part of a fluid disinfection process. This configuration is similar to that of FIG. 1f except connector 150 is attached to port 81 and connector 350 is attached to port 346.

Figure 2:
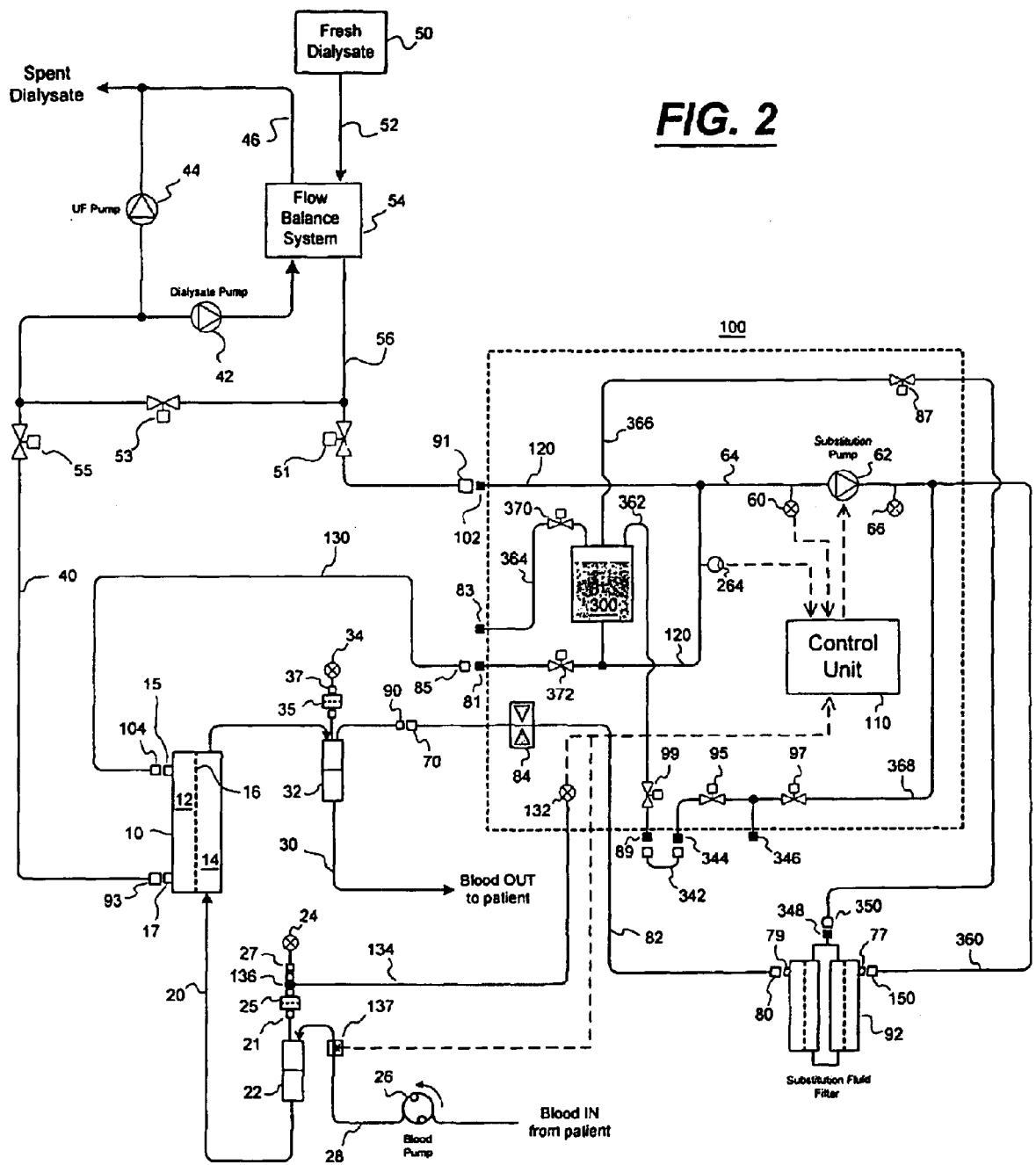
FIG. 2 is a schematic illustration of a diafiltration delivery module and sterilizing filter configured with a dialysis machine for diafiltration treatment in accordance with an embodiment of the invention using a flow switch and pressure transducers as feedback control inputs for the substitution pump.

A second embodiment of the invention is described with reference to FIG. 2. The difference between this embodiment and the first embodiment is the manner in which dialysate flow and blood flow is sensed by the diafiltration delivery module 100. Here, dialysate flow rate is sensed by flow switch 264 instead of flow meter 68. The flow switch 264, may be a thermal flow switch, such as supplied by Intek, Inc., Wattersville, Ohio or a mechanical flow switch, such as supplied by Dwyer Instruments, Inc., Michigan City, Ind. The state of the flow switch 264, either ON or OFF, is then used as a control input to the control unit 110 to either enable or disable operation of the substitution pump 62. For blood flow sensing, one may detect when the blood pump 26 is ON or OFF by detecting the occurrence of pressure pulses in the extracorporeal circuit as the result of the peristaltic nature of the roller type blood pump 26. Two means of detecting pressure pulses may be used. First, as shown in FIG. 2, one may use a pressure transducer 132 that is in fluid (air) contact with one of the drip chamber pressure monitoring ports, such as the arterial pressure monitoring port 27 of the dialysis machine. This may be accomplished by inserting a tee device 136 between the monitoring port 27 and the disposable transducer protector 25. The tee 136 is connected to a conduit 134 that leads to a pressure transducer 132 located within the diafiltration delivery module 100. Second, an alternative to this configuration is a surface mounted pressure transducer 137 that is in direct contact with a portion of the bloodline tubing, such as tubing segment 28. The surface mounted pressure transducer 137 may be mounted in tubing clip such that the flexible tubing is partially flattened against the surface of transducer for better sensing of pressure pulses. An example of a surface pressure transducer is the Model AB transducer available from Data Instruments, Inc. Acton, Mass. For control purposes, the time interval between successive pressure pulses can be used as a feedback control input to the control unit 110. If no pulses are detected, or if the time period waiting for a next pulse exceeds a pre-set value, the substitution pump 62 can be turned OFF and the system put in a safe state. It should be apparent to those skilled in the art that this embodiment also overcomes the safety issues described above when either blood or dialysate flow is stopped during treatment while having a distinct advantage over the first embodiment using flow meters in that the cost can be reduced significantly.

Figure 3:
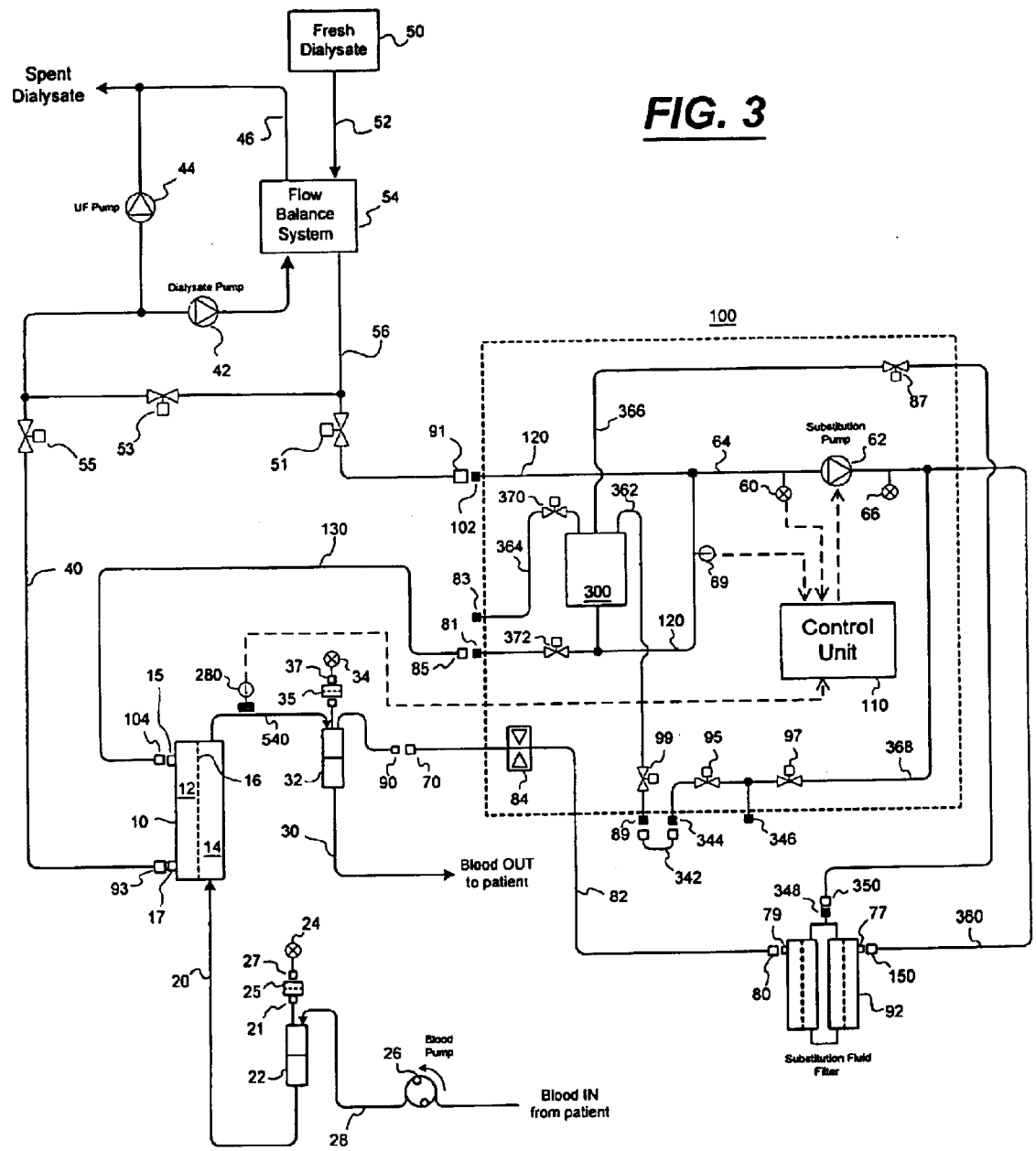
FIG. 3 is a schematic illustration of a diafiltration delivery module and sterilizing filter configured with a dialysis machine for diafiltration treatment in accordance with an embodiment using temperature decay as feedback control inputs for the substitution pump.

A third embodiment of the invention is illustrated in FIG. 3 which uses temperature decay measurements for monitoring dialysate flow rate and blood flow rate as opposed to flow meters, flow switches, or pressure transducers. Again operation is similar to the first embodiment with exception to the following. Dialysate and blood flow is indirectly measured using a temperature sensing device, such as thermistor, thermocouple, or infrared temperature sensor as are known in the art. For dialysate flow, the temperature sensing device 69 may placed in the fluid stream, such as a thermistor placed in conduit 120 or may be placed external to the fluid stream, such as an infrared temperature sensor that monitors the external surface of conduit 120. Since the dialysis machine supplies dialysate fluid at a controlled temperature, one can monitor the dialysate fluid temperature as a means to detect when the dialysis machine stops delivering fluid to the diafiltration delivery module, such as can occur when the machine goes into bypass. For example, if dialysate flow into the diafiltration delivery module 100 is interrupted, the fluid temperature within the module 100 will begin to cool. This decay in temperature, which may be determined simply as a change in temperature from a fixed set point (temperature decay) or as a change in temperature per unit time (decay rate), may then be used as a feedback control input to the control unit 110 that drives the substitution pump. For blood flow sensing, a blood temperature sensing device 280 may be used to monitor the extracorporeal circuit blood temperature. This may be accomplished by using a thermistor or thermocouple that is placed in direct contact with the outside surface of the blood tubing, such as accomplished by mounting the thermistor in a tubing clip that is affixed to the bloodline tubing or by using a non-contacting infrared temperature sensor that is directed at the blood tubing surface. By positioning the blood temperature sensing device 280 near the blood outlet of the dialyzer 10, such as the bloodline tubing segment 540, one can take advantage of the dialysis machine's ability to control the dialysate temperature. For example, blood temperature exiting dialyzer 10 should be substantially equal to the inlet dialysate temperature as the dialyzer 10 acts as an efficient heat exchanger. Again, since the dialysis machine supplies dialysate fluid at a controlled temperature, the blood temperature exiting the dialyzer will trend similarly with dialysate temperature. If the blood pump 26 stops in response to an alarm condition or is reduced to a low rate by the user, the blood in the extracorporeal circuit (excluding the dialyzer 10) will begin to cool. This decay in temperature, which may be determined simply as a change in temperature from a fixed set point relative to the dialysate temperature (temperature decay) or as a change in temperature per unit time relative to the dialysate temperature (decay rate), may then be used as a feedback control input to the control unit 110 that drives the substitution pump. Similarly to the above embodiments, it should be apparent to those skilled in the art that the system can be placed in a safe state in the event that either dialysate flow or blood flow is interrupted during operation of the invention.

Figure 4:
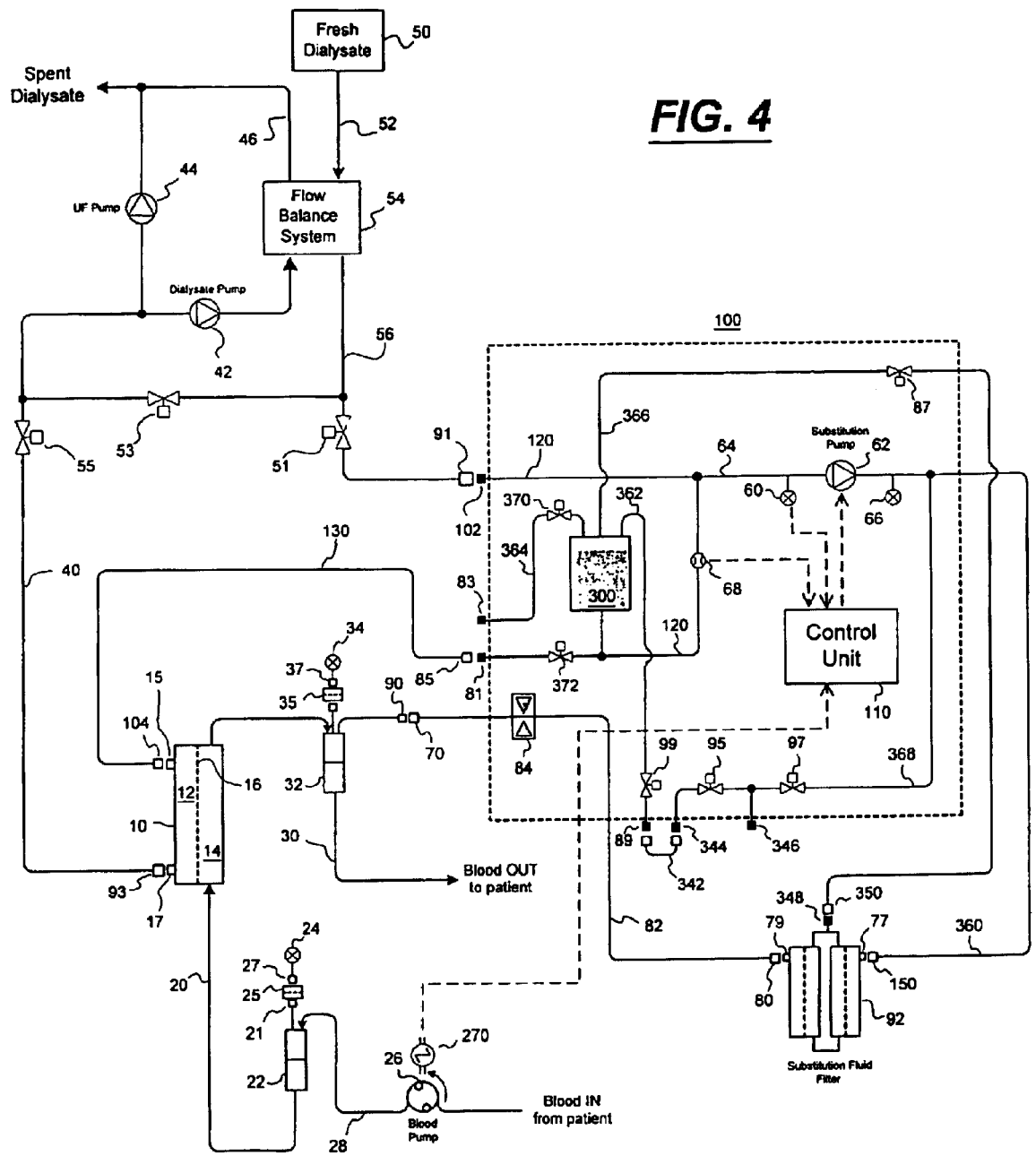
FIG. 4 is a schematic illustration of a diafiltration delivery module and sterilizing filter configured with a dialysis machine for diafiltration treatment in accordance with an embodiment using a tachometer positioned on the blood pump as a feedback control input for the substitution pump.

Reference is now made to FIG. 4 which shows yet another embodiment of the invention. In this embodiment, blood flow is sensed using a tachometer device 270 that measures the rotational speed of the blood pump 26. An example of a tachometer 270 that can be used is a non-contacting phototachometer such as supplied by Cole Parmer Instrument Company, Vernon Hills, Ill. Here, a piece of reflective tape is applied to a rotating member of the blood pump 26 while the phototachometer monitors the time interval between successive passes of the reflective tape. Operation is then similar to the second embodiment which looked at pressure pulses as a means to sense blood flow.

Figure 5:
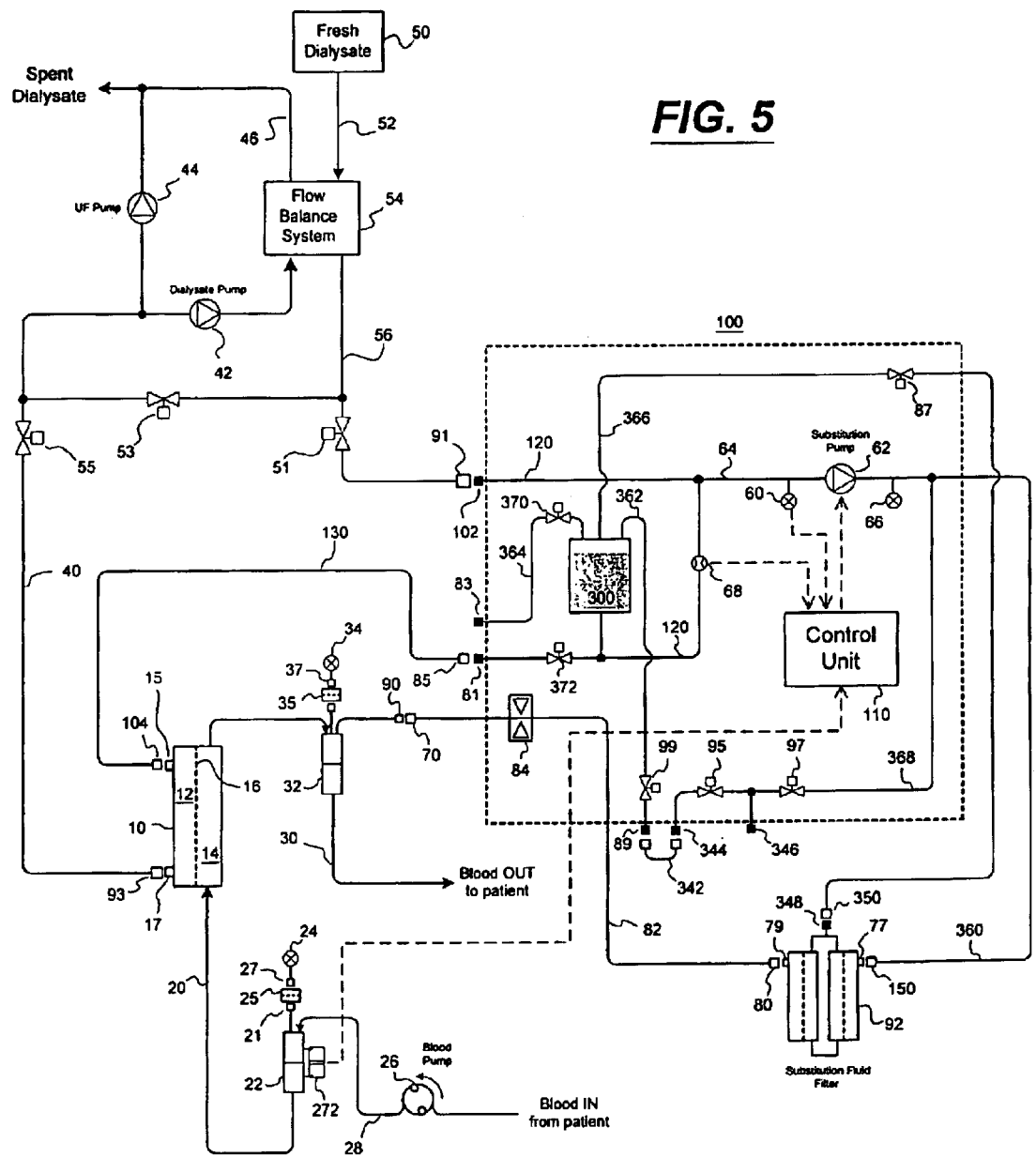
FIG. 5 is a schematic illustration of a diafiltration delivery module and sterilizing filter configured with a dialysis machine for diafiltration treatment in accordance with an embodiment using a photodiode array to monitor fluid level fluctuations in a drip chamber as a feedback control input for the substitution pump.

In a fifth embodiment of the invention, with reference now being made to FIG. 5, blood flow sensing is accomplished using a linear photodiode array 272, such as supplied by Integrated Vision Products AB, Linkoping, Sweden. The linear photodiode array 272 is positioned near one of the drip chambers, preferably the arterial drip chamber 22 of the extracorporeal blood circuit, such that it can be used to monitor relative changes in fluid level. For example, one may detect when the blood pump 26 is ON or OFF by detecting the occurrence of fluid level fluctuations in the drip chamber 22 as the result of the peristaltic nature of the roller type blood pump 26. For control purposes, the signal from the linear photodiode array 272 is sent to the control unit 110 as a feedback control input. If no fluid level fluctuations are detected, the substitution pump 62 can be turned OFF and the system put in a safe state.

Figure 6:
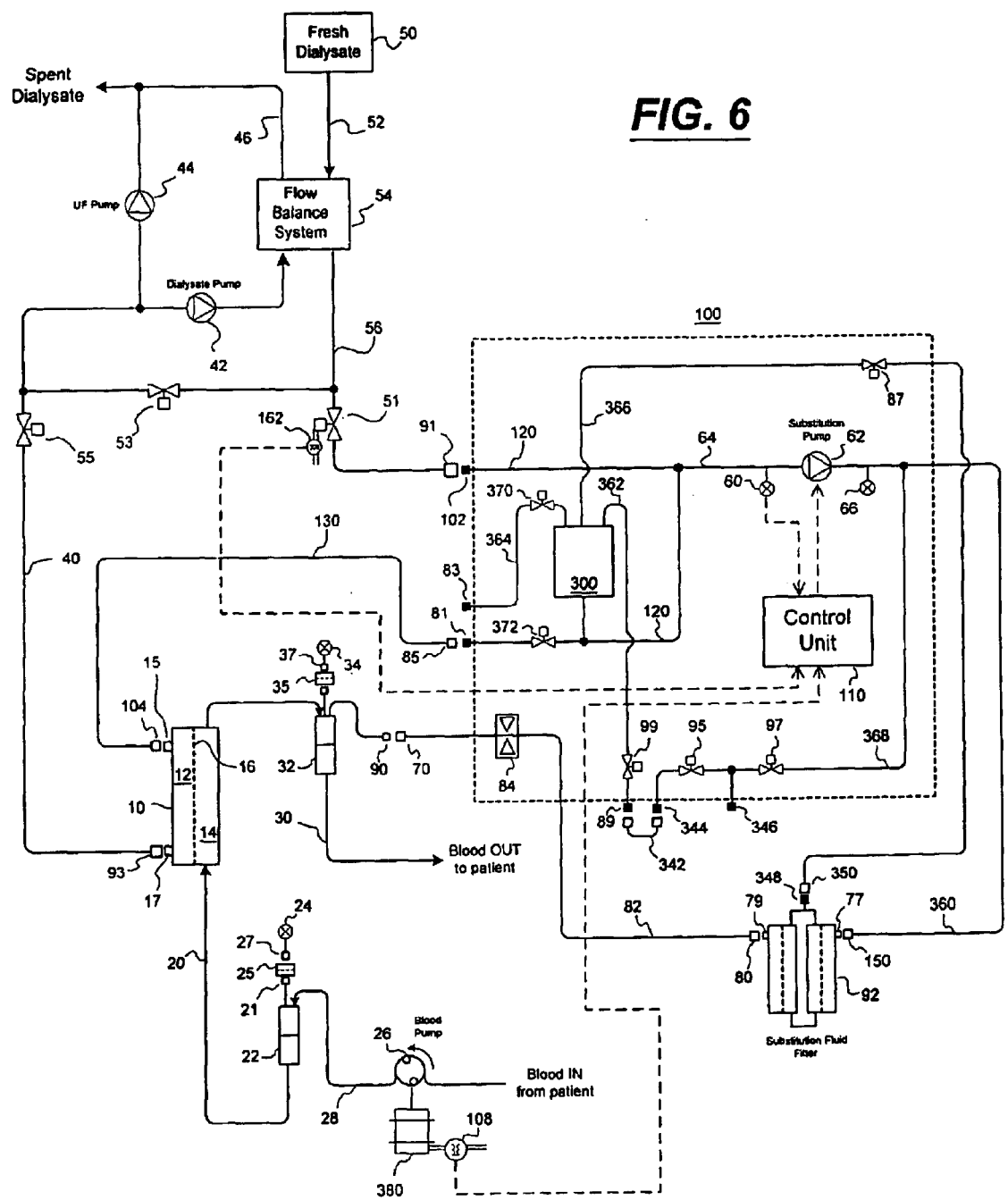
FIG. 6 is a schematic illustration of a diafiltration delivery module and sterilizing filter configured with a dialysis machine for diafiltration treatment in accordance with an embodiment using an inductive means to monitor electrical currents supplied to a dialysis machine valve and blood pump as feedback control inputs for the substitution pump.

Reference is now made to FIG. 6 showing a sixth embodiment of the invention. In this embodiment, dialysate and blood flow are indirectly sensed by inductively monitoring the current supplied to the inlet dialysate valve 51 and the motor that drives the blood pump 26. This may be accomplished by placing inductive current clamps 162 and 108 around the wires leading to the dialysate inlet valve 51 and the blood pump 26 respectively. An example of an inductive current clamp that can be used is the Fluke DMM current clamp supplied by Techni-Tool, Plymouth Meeting, Pa. Control of the diafiltration delivery module 100 may then accomplished by using the signals from the inductive current clamps 162 and 108 as feedback control inputs to the control unit 110. If a current is sensed flowing through the dialysate inlet valve 51 and through the blood pump 26, it can be assumed dialysate flow is passing through the diafiltration delivery module 110 and that blood flow is flowing through the extracorporeal circuit. When current is not detected by either inductive current clamp 162 or 108, the substitution pump 62 is turned OFF and the system is placed in a safe state.

Figure 7A:
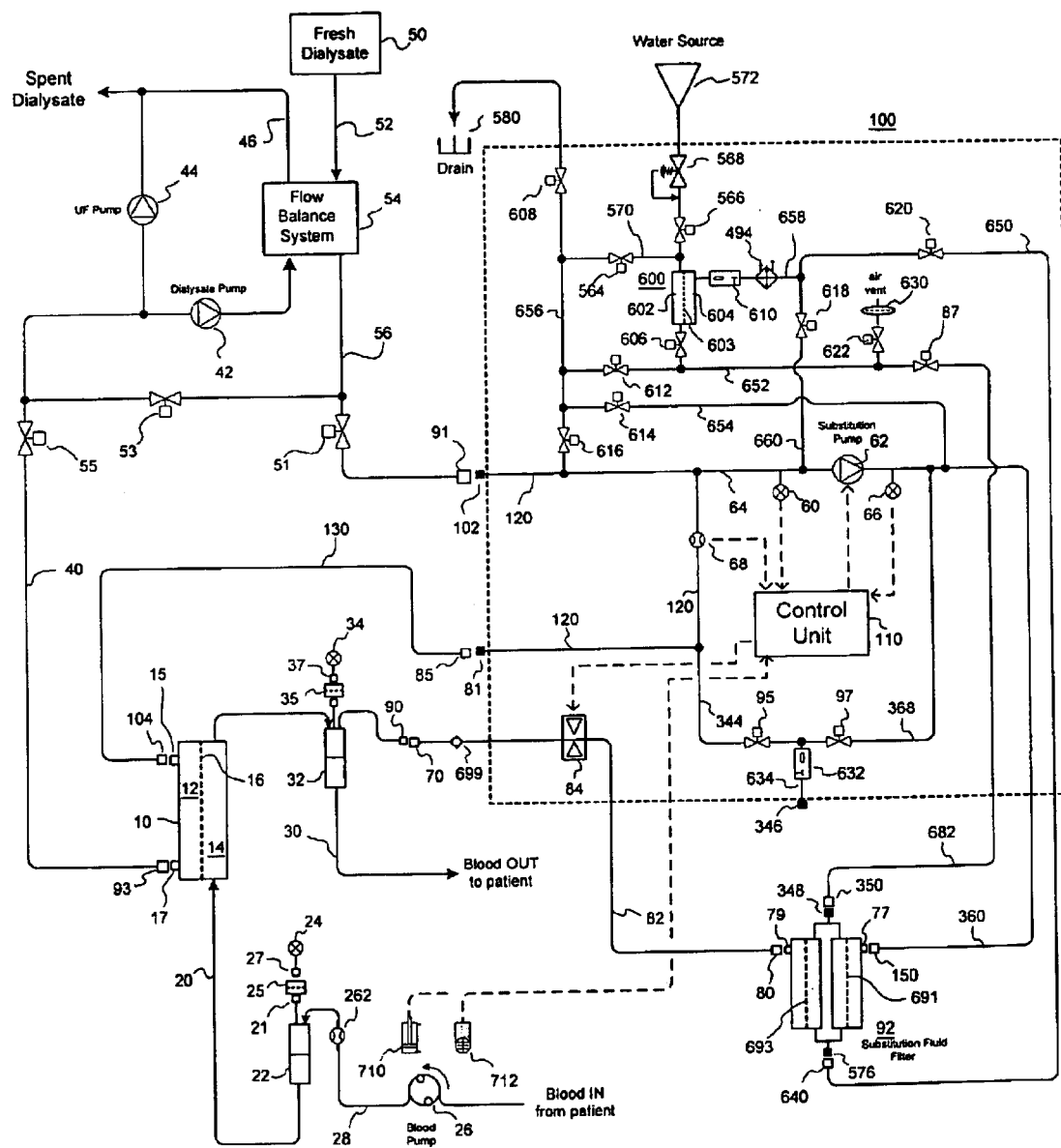
FIG. 7a is a schematic illustration of a diafiltration delivery module and sterilizing filter configured with a dialysis machine for diafiltration treatment in accordance with one embodiment using a vibration sensing device to monitor blood pump rotations as a feedback control input for the substitution pump.

In a seventh embodiment of the invention, with reference to FIG. 7a, a blood flow is indirectly sensed by detection of blood pump vibrations that occur when the peristaltic blood pump repeatedly compresses the blood pump segment with a roller mechanism as it rotates. Typically, the roller mechanism in the pump head is spring loaded such that the spring becomes more compressed during a portion of each blood pump rotation (i.e. when contacting the blood pump segment). Blood pump vibrations may be detected mechanically or acoustically. To detect vibrations mechanically, one may use a vibration transducer 710 that is in physical contact with the dialysis machine, preferably near the blood pump with the transducer axis lining up with the radial direction of the blood pump. An example of a vibration transducer that may be used is the A-118 vibration transducer available from CEC Vibration Products, Covina, Calif. To detect vibrations acoustically, one may use a sound detection device 712, such as a microphone, that in effect picks up sound vibrations from the blood pump as it rotates to propel blood through the extracorporeal circuit. When vibrations that are characteristic of blood pump rotation are not detected by either the vibration transducer 710 or the sound detection device 712, the substitution pump 62 is turned OFF and the system is placed in a safe state.

With continued reference to FIG. 7a, another aspect of the invention is shown whereby a check valve 699 is used in place of the optical blood sensor 382 described in the earlier embodiments. The check valve 699 is disposed in the infusion line conduit 82 that carries substitution fluid from the substitution fluid filter 92 to the extracorporeal circuit. The check valve 699, which permits flow in only one direction, serves to provide a secondary mechanism to prevent blood in the extracorporeal circuit from contaminating the substitution fluid filter 92. This together with the control aspect of the pinch valve 84 provide redundant safety mechanisms to prevent cross-contamination via the substitution filter and therefore enables the substitution filter to be used multiple times with different patients.

Figure 7B:
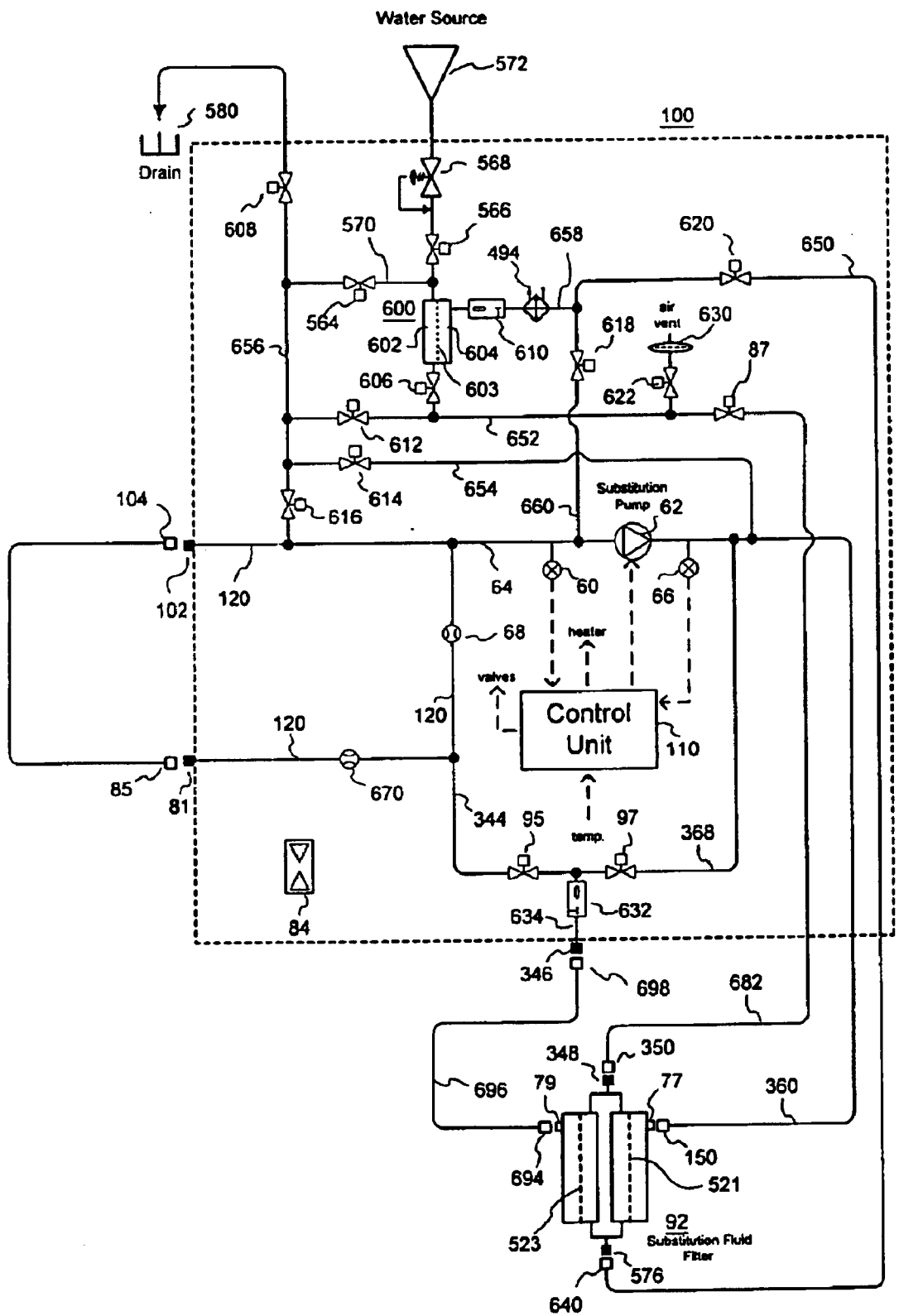
FIG. 7b is a schematic illustration of a diafiltration delivery module and sterilizing filter in a standalone configuration for testing and heat disinfection purposes in accordance with the embodiment.

Another aspect of ths embodiment is shown with reference to FIG. 7b. Here the diafiltration module 100 has been placed in a standalone configuration with the substitution fluid filter 92 remaining with the module for testing and disinfection. An advantage of this embodiment over the previous embodiment shown in FIG. 1e is that it does not require attachment of any additional fluid reservoirs (Such as 490, 470, and/or 472) to carry out the respective filter tests and disinfection procedures. Examples of how the various tests and disinfection procedures may be carried out are as follows. Priming of a new substitution filter is accomplished first by opening a water inlet valve 566 to introduce water from a source 572 which is typically an AAMI quality water as is known in the art. The water is then filtered through a water filter 600 that contains a semipermeable membrane 603. The water filter through a water filter 600 that contains a semipermeable membrane 603. The water filter removes bacteria, endotoxin, and other particulate that may be present in the incoming water stream. The filtered water exits the water filter 20 and passes through conduit 658. Valve 620 is opened to allow flow of the filtered water through conduit 650 that lead to the substitution fluid filter 92. Air in the inter-stage compartments (i.e. downstream of the first filter stage and upstream of the second filter stage) is pushed out of the filter and into conduit 682. Opening valves 87, 612, and 608 allows the air to pass out to the drain 580 via conduits 682 and 656. Next, valve 87 is closed such that the filter water is pushed across the semi-permeable membranes 521 and 523 which displaces the air in the respective upstream compartment of the first stage and the downstream compartment of the second stage. Opening valves 97, 614, and 608 then allows the displaced air to flow through conduits 360, 696, 368, 654, 656 and subsequently out to the drain 580 leaving the substitution filter 92 primed with filtered AAMI quality water. Testing the integrity of the water filter 600 may be performed as follows. Opening valves 606, 622, 618, 614, and 608 (all other valves being closed) and turning on the substitution pump 62 in the forward direction causes a negative pressure in the downstream compartment 604 of the water filter 600. This draws fluid across the semi-permeable membrane 603. To make up for the displaced fluid, air enters the fluid path through an air filter 630 and eventually fills the upstream compartment 602 of the water filter 600. The air filter 630 may be a hydrophobic filter as is known in the art and is used to prevent bacteria from entering into the fluid path of the module. The fluid being discharged by the substitution pump 62 flows out through conduits 654 and 656 that lead to the drain 580. After the water has been displaced from the upstream compartment 602, a negative pressure will build up in the conduit 660 leading to the substitution pump as air will not be able to pass through the water filter membrane 603 (assuming the filter is intact). Upon reaching a specified negative pressure, the substitution pump is turned OFF and the negative pressure measured by pressure transducer 60 may be monitored for pressure decay as discussed previously to verify integrity of the water filter. Integrity of the substitution filter may also be tested in a similar manner. For example, this may be accomplished by opening valves 622, 87, 97, 616 and 608 (all other valves closed) and turning ON the substitution pump 62 in the reverse direction. Here, air enters through the air filter 630 and displaces the water in conduit 682 and in the downstream compartment of the first stage of the substitution filter and the upstream compartment of the second stage of the substitution filter. The displaced fluid from the substitution filter flows through conduits 360, 696 and 368 leading back to the substitution pump 62. Fluid being discharged by the substitution pump 62 then flows through conduits 64 and 656 leading out to the drain 580. In a similar manner as described previously, a pressure decay test is performed that simultaneously verifies integrity of both filter stages of the substitution filter 92. Disinfection of the diafiltration module fluid path that includes both the water filter 600 and the substitution fluid filter 92 may be accomplished as follows. After priming and rinsing the fluid path with the filter water, the inlet water valve 566, the outlet drain valve 608, and the air vent valve 622 may be closed to seal off the fluid path from the external environment. The water inside the fluid path may then be recirculated through the module by turning ON the substitution pump 62 in the reverse direction and opening valves 620, 97, 616 and 654.

Next, the water may be heated to a desired temperature as it flows by a heating element 494. The heated water then flows through conduits 658 and 650 leading to the substitution filter 92. The heated water then passes through the filter membranes 521 and 523 and out through conduits 360 and 696. The temperature of the fluid exiting the substitution fluid filter may be monitored using a temperature sensor 632. This heated water then flows through conduit 368 and combines with the heated water flowing through conduit 360 leading back to the substitution pump 62. The discharged fluid from the substitution pump 62 then flows through conduits 64, 656 and 570 leading back to the upstream compartment 602 of the water filter 600. The water is again filtered across the semi-permeable membrane 603 and back to the heating element 494. It should be understood to those skilled in the art that manipulation of the valves of the fluid path would allow the entire fluid path of the module (excluding the water inlet line leading up to the water filter 600 and the air vent line containing the air filter 630) to be exposed to the heated water as a way to disinfect the module fluid path, the water filter 600, and the substitution filter 92. For example, to achieve a high level disinfection of the substitution filter, one may circulate heated fluid (preferable above 80° C.) for a set period of time. A chemical disinfection and/or cleaning process of the diafiltration module fluid path (without the substitution fluid filter 92) may be accomplished.

Figure 7C:
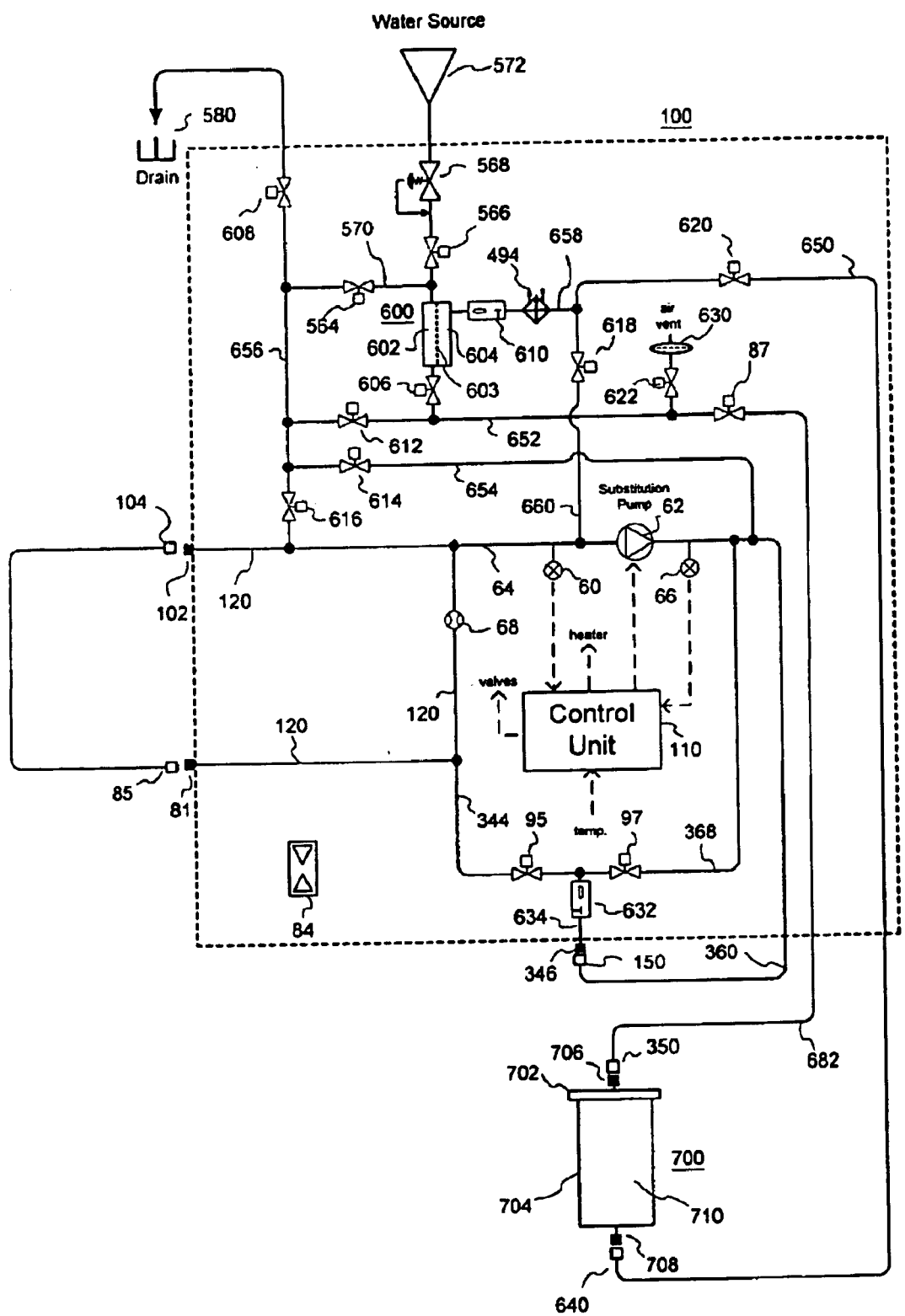
FIG. 7c is a schematic illustration of a diafiltration delivery module in a standalone configuration for disinfect dwell or storage purpose without a sterilzing filter in accordance with an embodiment.

With reference to FIG. 7c, the substitution fluid filter 92 has been removed and replaced with a container 700 containing chemical disinfect or cleaning solution 710. The container 700 may include a removable top 702 to allow one to reuse the container. The module 100 attaches to the container 700 by connecting connectors 350 and 640 to ports 706 and 708 respectively. Module connector 150 is attached module rinse port 346. As discussed previously with reference to FIG. 1e, one may recirculate fluid within the module to achieve a uniform concentration of disinfectant in most all parts of the fluid path. Rinsing the disinfectant out of the circuit may also be accomplished using fresh water 572 with the expelled fluid being sent out to the drain 580.

Figure 8:
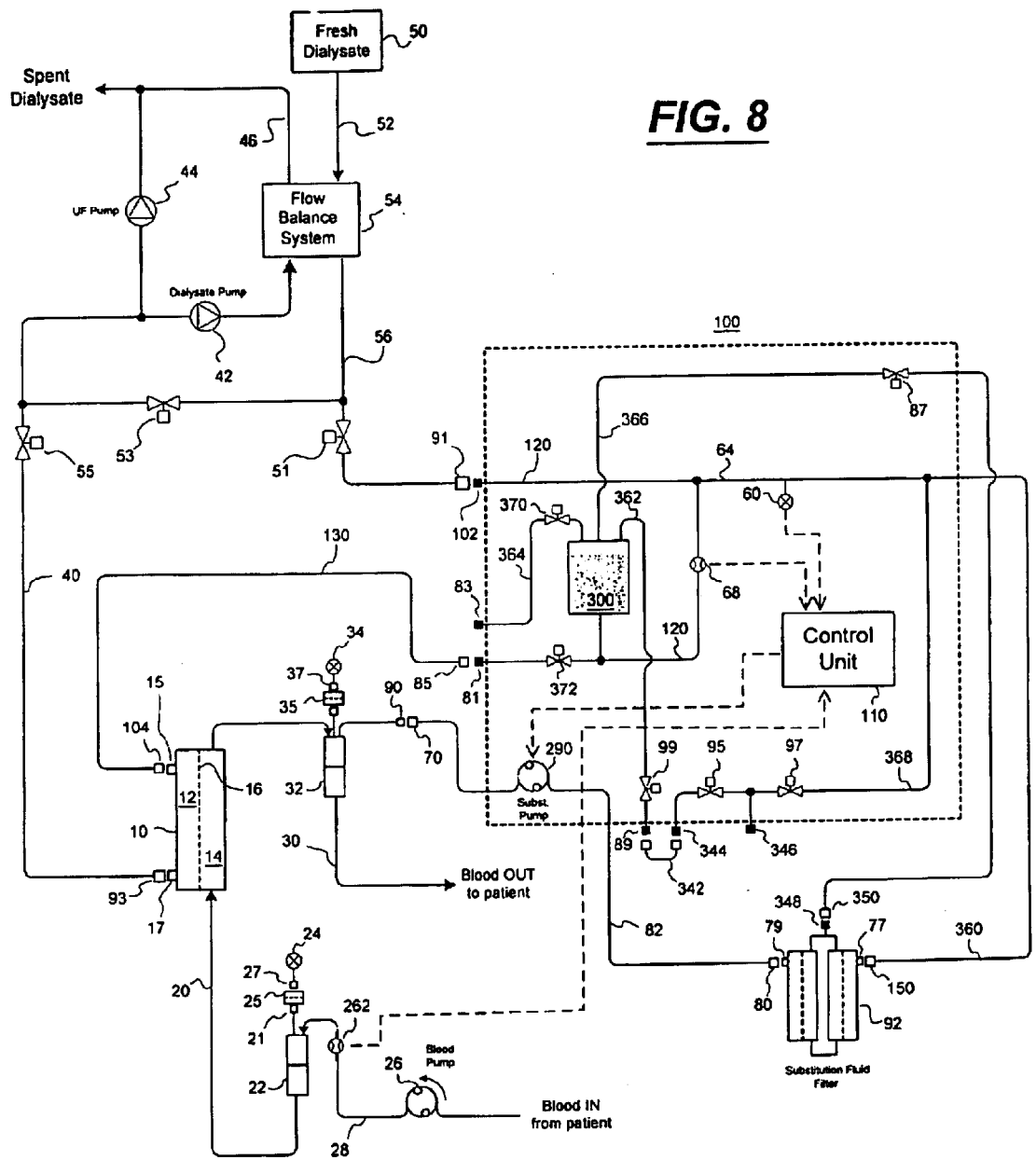
FIG. 8 is a schematic illustration of a diafiltration delivery module and sterilizing filter configured with a dialysis machine for diafiltration treatment in accordance with an embodiment using a occluding type substitution pump located on the infusion line between the sterilizing filter and the extracorporeal circuit.

Reference is now made to FIG. 8 showing an eighth embodiment of the invention. In this embodiment, an occluding type substitution pump 290 is used to deliver substitution fluid to the extracorporeal circuit. The configuration is similar to that of the first embodiment, except the substitution pump 290 has been moved to the downstream side of the substitution filter 92 and is used in place of the pinch valve. The occluding type pump 290 may be a peristaltic roller pump as is known in the art. This has the advantage of eliminating the need for the pinch valve and thus reducing the number of hardware components used in the diafiltration delivery module 100, however, this requires a special infusion line 82 containing a pump segment that fits the roller pump 290. Control of the substitution pump 290 is similar to that described in the above embodiments in that a means for detecting adequate flow of both dialysate and blood must be performed for safe operation of the device. In addition, one can prevent blood from contaminating the substitution filter 92 by only allowing the substitution pump 290 to turn in one direction (i.e. in the direction toward the extracorporeal circuit).

Figure 9:
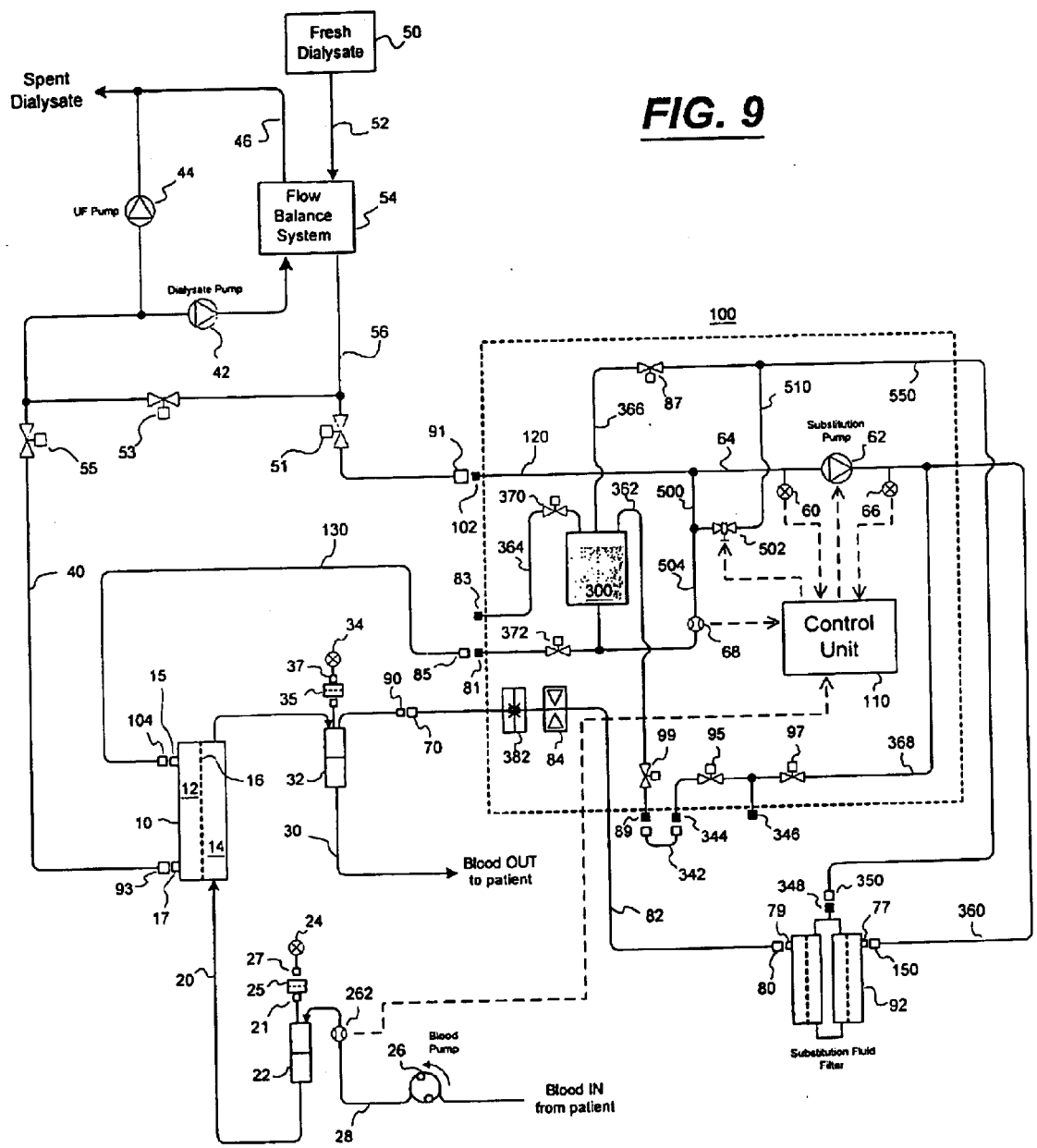
FIG. 9 is a schematic illustration of a diafiltration delivery module and sterilizing filter configured with a dialysis machine for diafiltration treatment in accordance with an embodiment that provides filtration of dialysate through a first filter stage and uses an adjustable throttling valve to control the rate of substitution fluid.

Reference is now made to FIG. 9 showing an ninth embodiment of the invention which adds the feature of filtering the entire dialysate stream prior to being delivered to the dialyzer cartridge 10 at its inlet port 15. The configuration is similar to the first embodiment (FIG. 1a) with the exception that a fluid conduit 510 has been added to provide a fluid connection between conduit 366 and what was conduit 120 in the previous embodiment. In the new conduit 510, a fluid throttling valve 502 has also been added. The throttling valve 502, for example, may be a proportioning valve such as supplied by South Bend Controls, South Bend, Ind. Filtration of the dialysate fluid during treatment may then be accomplished as follows. Dialysate fluid from the dialysis machine flows into the diafiltration delivery module 100 and flows through conduit 120. Initially the pinch valve 84 is closed to prevent substitution fluid from flowing out of conduit 82. This allows the dialysate flow rate delivered by the dialysis machine to be sensed by flow meter 68. This dialysate flow rate reading is then used as a basis for setting the substitution flow rate which is further described below. The aperture of the throttling valve 502 and the speed of the substitution pump 62 are each set to an initial setting. The substitution pump may be set such the its flow rate equals or exceeds the flow rate of the base dialysate fluid flow rate measured above. Next, the aperture of the throttling valve 502 is adjusted up or down until a pre-determined target pressure is observed at the discharge side of the substitution pump 62 via pressure transducer 66. The target pressure should be high enough to assure that substitution fluid in conduit 82 will flow in the direction of the extracorporeal circuit when the pinch valve 84 is opened. In other words, the target pressure should be sufficiently higher than an expected blood circuit pressure. With the substitution pump 62 running, flow of unfiltered dialysate fluid from conduit 120 will flow into conduit 64, through conduit 360, across the first filtering stage of the substitution filter 92. The filtered dialysate fluid then flows through conduit 550, into conduit 510 and through the throttling valve 502. If the flow rate through the substitution pump 62 is equal to the base dialysate flow, then all the filtered dialysate fluid flowing through conduit 510 will flow into conduit 504. If the flow rate through the substitution pump 62 is greater than the base dialysate flow, then a portion of filtered dialysate fluid flowing through conduit 510 will flow into conduit 500. This portion of filtered dialysate fluid is then mixed with the unfiltered dialysate from conduit 120 and recirculated back to the substitution pump 62 via conduit 64. In this fashion, only filtered dialysate fluid will flow into conduit 504.

In order to begin diafiltration, pinch valve 84 is opened to allow substitution fluid to flow from the diafiltration delivery module 100 to the extracorporeal circuit. When this occurs, the dialysate flow rate through conduit 504 will be reduced by an amount that is equal to the substitution fluid rate. By monitoring this change in dialysate flow rate, it is then possible to control substitution fluid flow rate using a feedback control loop that controls the aperture of the throttling valve 502. For example, to increase the substitution fluid flow rate, the control unit 110 can send a signal to the throttling valve 502 to reduce its aperture setting. This will have the effect of increasing the upstream side of the substitution fluid filter 92 to force more fluid across the filter and into the extracorporeal circuit. To decrease the substitution fluid flow rate, the control unit can enlarge its aperture setting which will have the opposite effect. An additional substitution pump control scheme based on a feedback control loop using pressure transducer 66 may be used to ensure that a minimum pressure is maintained on the discharge side of the substitution pump. For example, it may be necessary to boost the speed of the substitution pump to maintain a sufficient outlet pressure to assure blood does not back up into the substitution filter when the pinch valve 84 is in the open position.

Figure 10A:
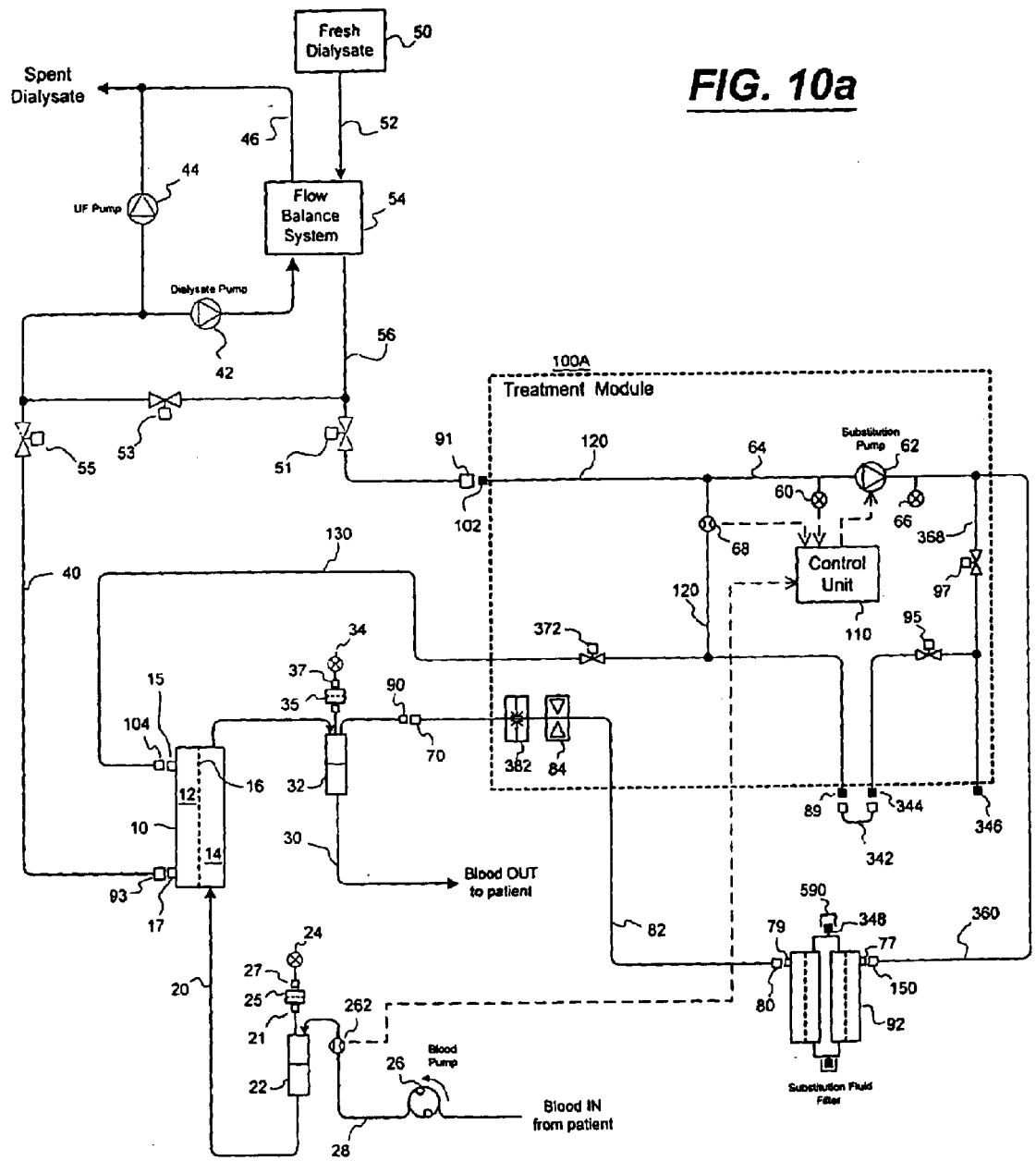
FIG. 10a is a schematic illustration of a treatment module portion of a diafiltration delivery module and a sterilizing filter configured with a dialysis machine for diafiltration treatment in accordance with an embodiment.
Figure 10B:
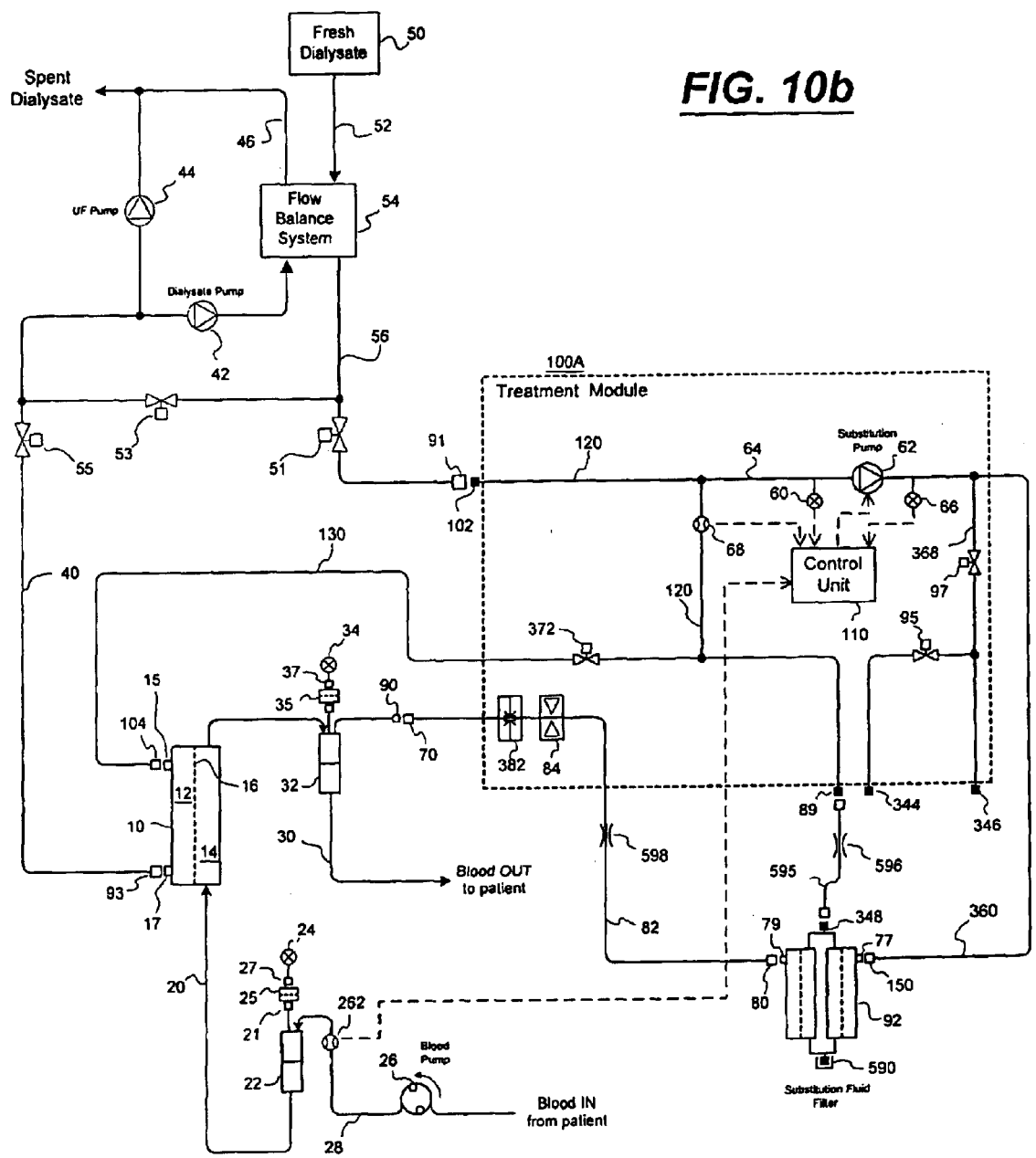
FIG. 10b is a schematic illustration of a treatment module portion of a diafiltration delivery module and a sterilizing filter configured with a dialysis machine for diafiltration treatment in accordance with an embodiment that provides filtration of the dialysate fluid prior to entering the dialyzer.
Figure 10C:
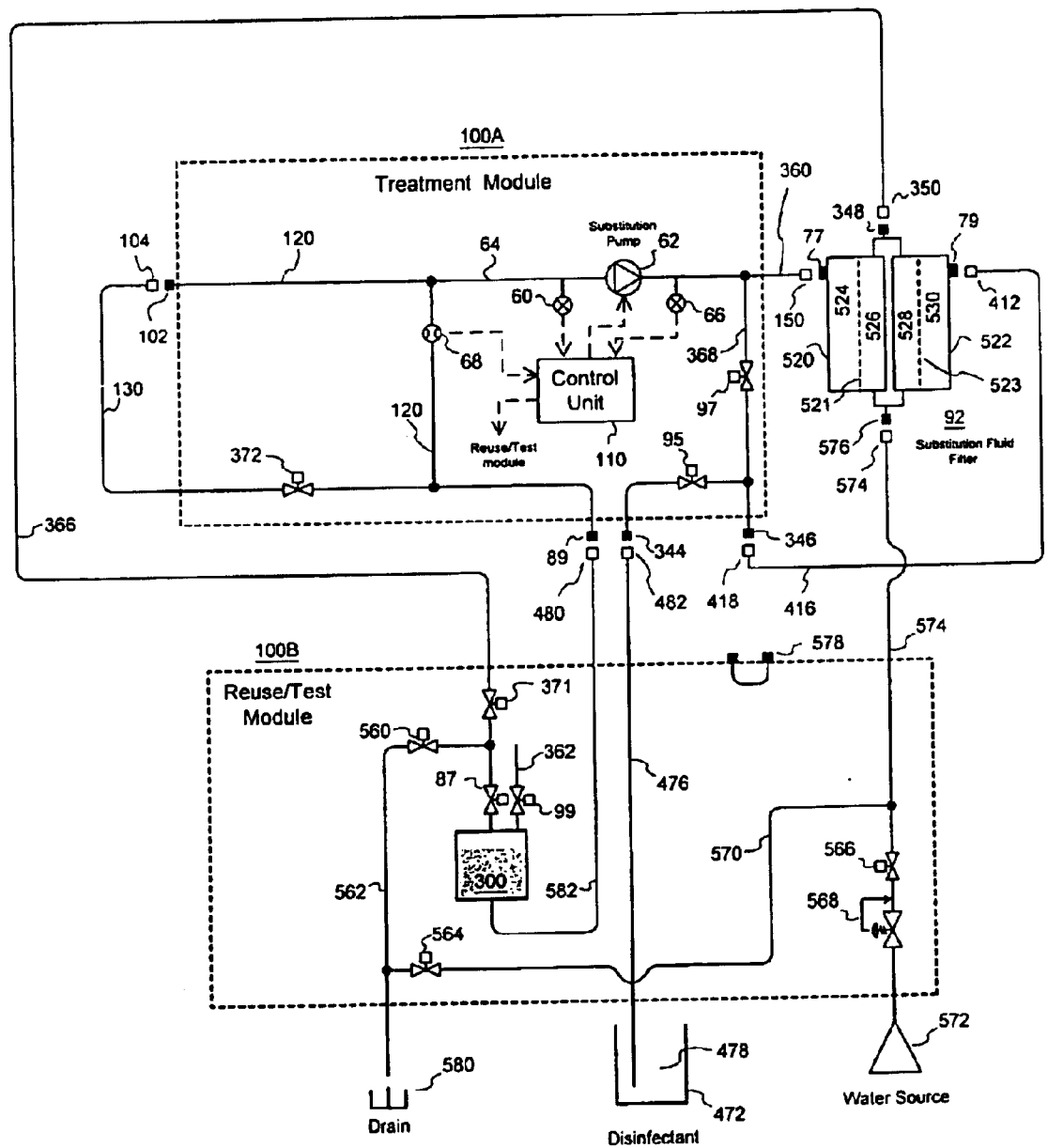
FIG. 10c is a schematic illustration of a diafiltration delivery module and a sterilizing filter in a standalone configuration whereby the diafiltration delivery module is composed of a treatment module portion and reuse/test module portion in accordance with an embodiment.

Reference is now made to FIGS. 10a, 10b and 10c showing a tenth embodiment of the invention. In this embodiment, the diafiltration delivery module has been separated into a treatment module portion 100A and a reuse/test module portion 100B. In order to perform diafiltration in conjunction with a dialysis machine, only the treatment module 100A is required as is shown in FIGS. 10a and 10b. In FIG. 10a, the treatment module 100A is configured for diafiltration without filtering the dialysate stream by a first filter stage of the substitution filter 92. In FIG. 10b, it is shown how to configure the treatment module 100A such that the dialysate stream is filtered by the first filtering stage of the substitution filter 92 prior to being delivered to the dialysate compartment of the dialyzer 10. In order to perform fluid path integrity tests, filter plugging and integrity tests, and disinfection of the substitution filter 92, the reuse/test module 100B is connected to the treatment module 100A in a standalone configuration as shown in FIG. 10c.

During treatment with the treatment module 100A, as shown in FIG. 10a, operation is similar to that described in the first embodiment with reference to FIG. 1a. For example, dialysate and blood flows are sensed via flow meters 68 and 262 respectively and if adequate, the substitution pump 62 draws a portion of the dialysate fluid stream and passes it through the substitution filter 92 before infusing into the extracorporeal circuit. It should be noted however, that the fluid reservoir 300 is not present in the treatment module 100A, and therefore it is not possible to generate substitution fluid for priming, fluid bolus, and rinseback purposes. Also, since conduit 366 is not present as part of the treatment module 100A, a filter cap 590 must be placed on the substitution filter 92 to prevent fluid from escaping out of the filter port 348.

As illustrated in FIG. 10b, it is possible to configure the treatment module 100A such that one can filter the dialysate stream through the first filtering stage of the substitution filter 92 prior to passing it through conduit 130 leading to the dialysate compartment 12 of dialyzer cartridge 10. This may be accomplished by adding a tubing conduit 595 that provides a fluid communication pathway between the substitution filter port 348 and port 89 on the treatment module 100A. The tubing conduit may contain a fluid restrictor 596, or may be of sufficient length and diameter to provide a given flow resistance (i.e. pressure drop) at a given flow rate through the tubing conduit 595. Operation of the treatment module 100A is as follows. Initially the pinch valve 84 is closed to prevent fluid from passing through conduit 82 leading to the extracorporeal circuit. The substitution pump 62 is turned on to a rate that is equal to or greater than the dialysate flow rate entering in from the dialysis machine. This redirects all incoming dialysate fluid from conduit 120, though conduit 64, into the substitution pump where it is pumped into conduit 360, across the first stage of the substitution filter 92, through conduit 595, and out into conduit 130 leading to the dialyzer 10. If the substitution pump 62 is running at a faster rate than the incoming dialysate stream, a portion of filtered dialysate fluid may be recirculated back to the substitution pump 62 via conduit 120 which is in fluid communication with conduit 64. If the flow resistance characteristics along the fluid path are known, for example the flow path that includes the first stage of the substitution filter 92 and tubing conduit 595, it is possible to calculate the pumping rate of the substitution pump 62 using pressure readings from pressure transducers 66 and 60. Likewise, if the substitution pump rate is known (such as if one is using a positive displacement type metering pump) one can calculate a pressure differential between transducers 66 and 60. For example, when the pinch valve 84 is closed such that no fluid is transferred across the second stage of the substitution filter 92, one can calculate the differential pressure as the product of the pumping rate and the fluid path flow resistance. Upon opening the pinch valve 84, one can monitor how much the differential pressure changes at pressure transducers 66 and 60 as a means to determine the substitution fluid flow rate being delivered to the extracorporeal circuit for diafiltration. For example, if no change in differential pressure occurs when opening the pinch valve 84, one can assume that no substitution fluid was generated and that all fluid passed through tubing conduit 595. If a change in the differential pressure is recorded by transducers 66 and 60, such that the differential pressure between 66 and 60 is less than before when pinch valve 84 was closed, one can assume that a portion of fluid was delivered to the extracorporeal circuit via conduit 82. By measuring the pressure differential, ΔP, where ΔP is defined as the pressure at transducer 66 minus the pressure at transducer 60 (i.e. $\Delta P = P_{66} - P_{60}$) at a given substitution pump 62 pumping rate (designated as $Q_{pump}$), one can calculate the delivered substitution fluid rate ($Q_{sub}$) as follows:

$$Q_{sub} = Q_{pump}(1 - \Delta P_{open}/\Delta P_{closed})$$

where $\Delta P_{open}$ is the pressure differential when pinch valve 84 is open, and $\Delta P_{closed}$ is the pressure differential when pinch valve 84 is closed.

Since $\Delta P_{closed}$ can be determined prior to treatment over a pre-set range of substitution pump speeds ($Q_{pump}$), or can be based on a theoretical calculation for a known fluid path resistance, one may then set up a feedback control loop to drive the substitution pump 62 based on inputs from pressure transducers 66 and 60 and a desired set point for $Q_{sub}$. It has also been discovered by the inventors that the addition of a fluid restrictor 598, such as located in the tubing conduit 82 between the outlet of the substitution filter and the extracorporeal circuit and preferably before the pinch valve 84, may improve the ability to control the substitution rate. For example, it has been found that better control is achieved when flow resistances of the fluid restrictors 596 and 598 are substantially greater than say the flow resistance across the first sterilizing filter stage of the substitution filter 92. Also, it is preferable that the combined flow resistance of the second sterilizing filter stage of the substitution filter 92 and the fluid restrictor 598 should be equal to or greater than the fluid resistance through tubing conduit 595 which may or may not contain a fluid restrictor 596. This based on an analysis that predicted a net change of actual substitution rate ($Q_{sub}$) upon a set change of the substitution pump rate ($Q_{pump}$).

Reference is now made to FIG. 10c which shows the configuration illustrating connections between the treatment module 100A, the reuse/test module 100B, and the substitution fluid filter 92 during test and disinfection operations. First, substitution filter caps 590 have been removed in order to attach connectors 350 and 574 to the filters ports 348, and 576 respectively. Conduit 366 provides a fluid pathway between connector 350 and the fluid reservoir 300 of the reuse/test module 100B in a similar manner as described with reference to FIG. 1e. Conduit 574 is connected to a water source 572, which is used for rinsing, priming and purging air out of the substitution filter 92 and the fluid paths of both modules 100A and 100B. The water source should be of suitable quality as known in the art, such as AAMI quality water used in hemodialysis and/or dialyzer reprocessing systems. A water inlet pressure regulating valve 568 and an inlet water valve 566 may be included, for example, to regulate water pressure in the two modules 100A and 100B. The substitution filter rinse line, now includes only a straight tubing conduit 416 with end connectors 418 and 412. Connector 412 is connected to the outlet substitution filter port 79 while connector 418 is connected to treatment module 100A rinse port 346. The treatment module shunt connector containing conduit 342 is removed and fluid conduits 476 and 582 are connected to rinse ports 344 and 89 via connectors 482 and 480 respectively. Conduit 476 provides a fluid communication pathway to a reservoir 472 which contains a concentrated disinfectant solution 478. Conduit 582 provides a fluid communication pathway to the bottom of an internal fluid reservoir 300 of the reuse/test module 100B. Two additional conduits are present in the reuse/test module 100B. These are conduits 562 and 570. Conduit 562 tees into conduit 366 and thus provides a fluid communication pathway to a drain 580. Conduit 570 provides a fluid path between conduits 574 and 562. Test and disinfect operations are described more fully below.

Rinsing and/or purging air out of the substitution filter 92 and fluid path circuit (but excluding the disinfectant line 476 and air vent line 362) is accomplished by first opening valves 566, 371 and 560 (all other valves are closed) to allow water to flow through conduit 574, into substitution filter compartments 526 and 528, through conduits 366 and 562, and out to drain 580. Next, valves 97, 372, and 87 can be opened while closing valve 371. Then by turning the substitution pump ON in the reverse direction (outlet toward conduit 64), flow of water will occur across the two semi-permeable membranes 521 and 523 from compartments 526 and 528 and into compartments 524 and 530. From here, flow will proceed into conduit 360 which is in parallel with conduits 416 and 368 that lead back to the substitution pump 62. Fluid then flows through conduit 64, where it is split into the two parallel conduits 120 and 130 that later rejoin and flow through conduit 582 leading to the fluid reservoir 300. Any air in the fluid reservoir 300 is purged out of the top and through conduit 562 going out to drain 580. Rinsing and purging conduit 570 is accomplished by opening valves 566 and 564 (all others being closed) to shunt water from the higher pressure water inlet side to the lower pressure drain side.

A fluid path integrity test to verify that the fluid path and connections to the substitution filter are intact can be performed in a manner very similar to that described earlier with reference to FIG. 1e. For example, one can close all valves except valves 97, 371 and 372 and turn ON the substitution pump 62 in the forward direction for a period of time or until a certain pressure is observed at the discharge pressure transducer 66. Here, a positive pressure generally develops in the substitution filter cartridge 92 while a negative pressure is generated in the fluid reservoir 300. At the end of the pressurizing period, the substitution pump 62 may be turned OFF and, after a specified stabilization period, the control unit 110 may monitor the rate of pressure decay over a set test period. Any fluid path leaks may then be detected when the measured pressure decay exceeds a predetermined limit. Similarly, a second integrity test may be performed with the substitution pump 62 operated in the reverse direction. Here, a positive pressure generally develops in the fluid reservoir 300, while a negative pressure is generated in the substitution filter cartridge 92.

Next, a water permeability test may be performed as a means to monitor the degree of plugging of the first filter stage 520 of the substitution fluid filter 92. This may be accomplished by running the substitution pump 62 in the forward direction at a specified rate with all valves closed except for valves 87, 371 and 372. Fluid then runs from the substitution pump 62, through conduit 360 and across the first stage 520 of the substitution filter which includes the semi-permeable membrane 521. Next it passes through conduit 366, into reservoir 300, and out through conduit 582 which feeds into conduit 120. It is then returned to the substitution pump 62 via conduit 64. By monitoring pressures at pressure transducers 60 and 66, one may determine the degree of plugging by comparing the resulting pressure differential relative to that of a new substitution filter.

A substitution filter membrane integrity test that tests both filter stages 520 and 522 simultaneously may also be performed as follows. First, the fluid reservoir 300 must be partially emptied. This may be accomplished by opening valves 99, 371 and 560 (all other valves closed) and turning ON the substitution pump 62 in the forward direction. As fluid is drawn out of the fluid reservoir 300 by action of the substitution pump, air will enter the fluid reservoir 300 through the vented conduit 362. Fluid removed from the reservoir will then flow out through conduit 582, into conduit 120, and sequentially through conduit 64, conduit 360, compartment 524, compartment 526, conduit 526, and conduit 562 where it goes out to drain 580. Next, valves 87, 371 and 97 are opened, valve 560 is closed, and the substitution pump 62 turned ON in a reverse direction. Now a negative pressure is simultaneously generated at the inlet and outlet ports, 77 and 79, of the substitution filter 92. This will in turn draw fluid across both filter membranes 521 and 523 such that fluid flows from the first downstream compartment 526 into the first upstream compartment 524 and from the second upstream compartment 528 into the second downstream compartment 530. Because the first downstream compartment 526 and the second upstream compartment 528 is fluid communication with the top of the fluid reservoir 300 via conduit 366, air in the top of the partially full fluid reservoir 300 will flow into conduit 366 and eventually into the filter compartments 526 and 528. When the fluid in compartments 526 and 528 is completely displaced by the air, the negative pressure as sensed by pressure transducer 66 should become more negative since air should not be able to cross the semi-permeable membranes 521 and 523, assuming they are intact. Upon reaching a specified negative pressure, the substitution pump 62 may be turned OFF provided it is an occluding type pump. After a specified stabilization period, the control unit 110 may monitor the rate of pressure decay over a set test period. Any substitution filter integrity leaks may then be detected when the measured pressure decay exceeds a predetermined limit as is known in the art as a pressure decay test. Upon passing the pressure decay test, refilling the substitution filter compartments 526 and 528 with fluid may be accomplished in a similar manner described above for rinsing and/or purging air out of the substitution filter and fluid path.

With continued reference to FIG. 10c, fluid path of modules 100A and 100B and the substitution filter 92 may be loaded with a disinfectant solution for disinfection of the fluid path and substitution filter. For a chemical disinfection, a concentrated disinfecting solution 478 may be placed into the fluid reservoir 472. This fluid may be drawn into the fluid path by opening valves 95, 97, 87 and 560 (all other valves closed), and turning on the substitution pump 62 in the reverse direction with flow leading into conduit 64.

Provided the substitution pump 62 is an occluding type pump, such as a metering pump, a specified volume of concentrated disinfecting solution 478 can be pumped into the fluid path as necessary to achieve a desired final concentration upon mixing with water already contained in the fluid path. In addition, it is possible as part of this step or a previous step to purge air out of the fluid reservoir 300 prior to the starting the next step. Mixing may be accomplished by opening valves 87, 371 and 97 (all other valves closed) and turning the pump ON in the reverse direction. This forms a recirculating loop that pumps fluid through the circuit as follows. From the substitution pump 62, fluid is pumped into conduit 64 and into parallel conduits 120 and 130. Next it rejoins and passes through conduit 582 and into the fluid reservoir 300. Fluid in the reservoir is pushed out the top and into conduit 366 that leads to the substitution fluid filter compartments 526 and 528. This fluid is then simultaneously pushed across the semi-permeable membranes 521 and 523 and into compartments 524 and 530. Fluid from compartment 524 flows into conduit 360 while fluid in compartment 530 flows into conduit 416 that leads to conduit 368. Here it is rejoined with the fluid in conduit 360 that leads back to the substitution pump 62. After a period of time, the fluid in this recirculating loop will become mixed thus having a uniform concentration throughout. To complete exposing the fluid path to the disinfecting solution, valves 99 and 564 are opened (all others closed) with the substitution fluid pump 62 turned ON in the forward direction. Due to the pumping action, air will enter the fluid reservoir 300 through conduit 362 as the disinfectant solution is drawn toward the substitution pump 62 via conduits 582, 120, and 64. The pump will then push the fluid into compartments 524 and 530, across the semi-permeable membranes 521 and 523, into compartments 526 and 528, out through conduit 574, where it passes through conduit 570, and out to drain 580. Upon completion, the substitution filter may be removed from the treatment and test modules 100A and 100B for storage, such as may be necessary to satisfy a minimum disinfectant dwell period. In removing the substitution filter 92, connectors 150 and 418 are detached from ports 77 and 346 and reconnected such that 150 connects to port 346 and 418 connects to port 77 (not shown). Connectors 350 and 574 are detached from the substitution filter and are placed on rinse ports 578. Caps, such as indicated by 590 in FIG. 10a, can then be placed on reuse test module 100B dual rinse ports 578 to contain the fluid in the substitution fluid filter 92.

It will be appreciated by persons skilled in the art to which this invention pertains that the invention is not limited to the preferred embodiments and configurations described above and with reference to the accompanying drawings.

What is claimed is:

1. In a blood dialysis system including a dialysis machine and an extracorporeal circuit including a dialyzer, a diafiltration module that is an independent standalone unit relative to the dialysis machine and the extracorporeal circuit and is adapted to be detachably connected to at least one of the dialysis machine and the extracorporeal circuit, the diafiltration module comprising:

a first conduit having a first end and an opposing second end, the first end for receiving a dialysate fluid from the dialysis machine and the second end for discharging the dialysate fluid to the dialyzer;

a second conduit in selective communication with the first conduit such that the second conduit selectively receives a diverted amount of the dialysate fluid from the first conduit, the second conduit communicating with at least one sterilizing filter for filtering the diverted amount of the dialysate fluid to produce a substitution fluid, wherein one end of the second conduit is configured to deliver the substitution fluid to the extracorporeal circuit;

a control unit responsive to a first detected characteristic of one of the dialysate fluid flowing within the first conduit and the diverted dialysate fluid flowing within the second conduit, the control unit being configured to prevent flow of substitution fluid to the extracorporeal circuit by controlling flow of the diverted dialysate fluid within the second conduit in the control module when at least the first detected characteristic meets a prescribed criteria a pinch valve disposed within the second conduit for controlling the flow of the substitution fluid through the second conduit, the pinch valve being in communication with the control unit.

2. The diafiltration module according to claim 1, wherein the control unit is responsive to a second detected characteristic of blood within the extracorporeal circuit, the second detected characteristic being a flow rate of the blood, wherein the control unit is configured to prevent flow of substitution fluid to the extracorporeal circuit by controlling flow of the diverted dialysate fluid within the second conduit in the control module when at least the second detected characteristic meets a prescribed criteria.

3. The diafiltration module according to claim 2, further including:

a first flow meter disposed within the first conduit for detecting a flow rate of the dialysate fluid within the first conduit, wherein the detected flow rate comprises the first detected characteristic, the first flow meter in communication with the control unit; and a second flow meter disposed within the extracorporeal circuit for detecting a flow rate of the blood, the second flow meter in communication with the control unit, wherein the detected flow rate of blood comprises the second detected characteristic.

4. The diafiltration module according to claim 1, further including:

a pressure transducer disposed within the second conduit downstream of the substitution fluid pump for detecting a pressure within the second conduit, the pressure being the first detected characteristic, the pressure transducer in communication with the control unit, wherein the control unit controls the position of the pinch valve based on input received from the substitution fluid pump and the pressure transducer.

5. The diafiltration module according to claim 4, further including:

an optical sensor disposed within the second conduit downstream of the at least one sterilizing filter for detecting transmittance of fluid contained in the second conduit downstream of the at least one sterilizing filter, the optical sensor being in communication with the control unit, wherein the optical sensor includes a light source and a photo-detector to detect a loss of transmittance of light through the fluid contained with the second conduit downstream of the at least one sterilizing filter, wherein the control unit controls the position of the pinch valve also based on input received from optical sensor.

6. The diafiltration module according to claim 4, wherein the control unit signals the pinch valve to open when (a) the substitution fluid pump is operating and the diverted fluid is pumped within the second conduit towards the at least one sterilizing filter and (b) the pressure transducer detects a minimum pressure that assures that the substitution fluid flow remains in a forward direction into the extracorporeal circuit when the pinch valve opens.

7. The diafiltration module according to claim 5, wherein the pinch valve is closed by the control unit when the optical sensor detects blood in the second conduit.

8. In a blood dialysis system including a dialysis machine and an extracorporeal circuit including a dialyzer, a diafiltration module that is an independent standalone unit relative to the dialysis machine and the extracorporeal circuit and is adapted to be detachably connected to at least one of the dialysis machine and the extracorporeal circuit, the diafiltration module comprising:
    a first conduit having a first end and an opposing second end; the first end for receiving a dialysate fluid from the dialysis machine and the second end for discharging the dialysate fluid to the dialyzer;
    a second conduit in selective communication with the first conduit such that the second conduit selectively receives a diverted amount of the dialysate fluid from the first conduit, the second conduit communicating with at least one sterilizing filter for filtering the diverted amount of the dialysate fluid to produce a substitution fluid, wherein one end of the second conduit is configured to deliver the substitution fluid to the extracorporeal circuit;
    a control unit responsive to a first detected characteristic of one of the dialysate fluid flowing within the first conduit and the diverted dialysate fluid flowing within the second conduit, the control unit being configured to prevent flow of substitution fluid to the extracorporeal circuit by controlling flow of the diverted dialysate fluid within the second conduit in the control module when at least the first detected characteristic meets a prescribed criteria
    a substitution fluid pump disposed within the second conduit for diverting the amount of the dialysate fluid from the first conduit to the second conduit, the substitution fluid pump being in communication with the control unit; and
    a flow switch disposed within the first conduit for detecting a flow rate within the first conduit, wherein the flow rate is the first detected characteristic, the flow switch being positionable between an ON position and an OFF position with the position of the flow switch being inputted to the control unit for controlling the operation of the substitution fluid pump.

9. The diafiltration module according to claim 8, wherein the flow switch comprises one of a thermal flow switch and a mechanical flow switch.

10. In a blood dialysis system including a dialysis machine and an extracorporeal circuit including a dialyzer, a diafiltration module that is an independent standalone unit relative to the dialysis machine and the extracorporeal circuit and is adapted to be detachably connected to at least one of the dialysis machine and the extracorporeal circuit, the diafiltration module comprising:
    a first conduit having a first end and an opposing second end, the first end for receiving a dialysate fluid from the dialysis machine and the second end for discharging the dialysate fluid to the dialyzer;
    a second conduit in selective communication with the first conduit such that the second conduit selectively receives a diverted amount of the dialysate fluid from the first conduit, the second conduit communicating with at least one sterilizing filter for filtering the diverted amount of the dialysate fluid to produce a substitution fluid, wherein one end of the second conduit is configured to deliver the substitution fluid to the extracorporeal circuit;
    a control unit responsive to a first detected characteristic of one of the dialysate fluid flowing within the first conduit and the diverted dialysate fluid flowing within the second conduit, the control unit being configured to prevent flow of substitution fluid to the extracorporeal circuit by controlling flow of the diverted dialysate fluid within the second conduit in the control module when at least the first detected characteristic meets a prescribed criteria, wherein the control unit is responsive to a second detected characteristic of blood within the extracorporeal circuit, the second detected characteristic being a flow rate of the blood, wherein the control unit is configured to prevent flow of substitution fluid to the extracorporeal circuit by controlling flow of the diverted dialysate fluid within the second conduit in the control module when at least the second detected characteristic meets a prescribed criteria; and
    a substitution fluid pump disposed within the second conduit for diverting the amount of the dialysate fluid from the first conduit to the second conduit, the substitution fluid pump being in communication with the control unit;
    wherein the dialysis machine includes a blood pump disposed within the extracorporeal circuit for transporting blood through the extracorporeal circuit; and
    wherein the second detected characteristic of blood comprises pressure pulses in the extracorporeal circuit, the detection of pressure pulses being inputted to the control unit to signal whether the blood pump is operating below a predetermined threshold value, the pressure pulses being processed by the control unit as feedback control input for controlling operation of the substitution pump.

11. The diafiltration module according to claim 10, wherein the extracorporeal circuit includes
    a drip chamber disposed therein, the drip chamber having one or more pressure monitoring ports; and
    a pressure transducer that is in fluid contact with one of the pressure monitoring ports of the drip chamber, the pressure transducer detecting the pressure pulses in the extracorporeal circuit.

12. The diafiltration module according to claim 10, further including:
    a surface mounted pressure transducer that is in contact with a portion of a conduit defining the extracorporeal circuit, the surface mounted pressure transducer detecting the pressure pulses in the extracorporeal circuit.

13. The diafiltration module according to claim 10, wherein the control unit monitors a time interval between successive pressure pulses detected in the extracorporeal circuit such that the substitution fluid pump is turned to the OFF position by the control unit if one of (a) no pressure pulses are detected and (b) if the timer interval exceeds a predetermined value.

14. In a blood dialysis system including a dialysis machine and an extracorporeal circuit including a dialyzer, a diafiltration module that is an independent standalone unit relative to the dialysis machine and the extracorporeal circuit and is adapted to be detachably connected to at least one of the dialysis machine and the extracorporeal circuit, the diafiltration module comprising:

a first conduit having a first end and an opposing second end, the first end for receiving a dialysate fluid from the dialysis machine and the second end for discharging the dialysate fluid to the dialyzer;

a second conduit in selective communication with the first conduit such that the second conduit selectively receives a diverted amount of the dialysate fluid from the first conduit, the second conduit communicating with at least one sterilizing filter for filtering the diverted amount of the dialysate fluid to produce a substitution fluid, wherein one end of the second conduit is configured to deliver the substitution fluid to the extracorporeal circuit:

a control unit responsive to a first detected characteristic of one of the dialysate fluid flowing within the first conduit and the diverted dialysate fluid flowing within the second conduit the control unit being configured to prevent flow of substitution fluid to the extracorporeal circuit by controlling flow of the diverted dialysate fluid within the second conduit in the control module when at least the first detected characteristic meets a prescribed criteria, wherein the control unit is responsive to a second detected characteristic of blood within the extracorporeal circuit, the second detected characteristic being a flow rate of the blood, wherein the control unit is configured to prevent flow of substitution fluid to the extracorporeal circuit by controlling flow of the diverted dialysate fluid within the second conduit in the control module when at least the second detected characteristic meets a prescribed criteria, wherein the first detected characteristic is detected by a temperature decay measurement of at least one of the dialysate fluid in the first conduit and the diverted dialysate fluid in the second conduit.

15. In a blood dialysis system including a dialysis machine and an extracorporeal circuit including a dialyzer, a diafiltration module that is an independent standalone unit relative to the dialysis machine and the extracorporeal circuit and is adapted to be detachably connected to at least one of the dialysis machine and the extracorporeal circuit, the diafiltration module comprising:

a first conduit having a first end and an opposing second end, the first end for receiving a dialysate fluid from the dialysis machine and the second end for discharging the dialysate fluid to the dialyzer;

a second conduit in selective communication with the first conduit such that the second conduit selectively receives a diverted amount of the dialysate fluid from the first conduit, the second conduit communicating with at least one sterilizing filter for filtering the diverted amount of the dialysate fluid to produce a substitution fluid, wherein one end of the second conduit is configured to deliver the substitution fluid to the extracorporeal circuit;

a control unit responsive to a first detected characteristic of one of the dialysate fluid flowing within the first conduit and the diverted dialysate fluid flowing within the second conduit, the control unit being configured to prevent flow of substitution fluid to the extracorporeal circuit by controlling flow of the diverted dialysate fluid within the second conduit in the control module when at least the first detected characteristic meets a prescribed criteria, wherein the control unit is responsive to a second detected characteristic of blood within the extracorporeal circuit, the second detected characteristic being a flow rate of the blood, wherein the control unit is configured to prevent flow of substitution fluid to the extracorporeal circuit by controlling flow of the diverted dialysate fluid within the second conduit in the control module when at least the second detected characteristic meets a prescribed criteria, wherein the second detected characteristic is detected by a temperature decay measurement of the blood.

16. In a blood dialysis system including a dialysis machine and an extracorporeal circuit including a dialyzer, a diafiltration module that is an independent standalone unit relative to the dialysis machine and the extracorporeal circuit and is adapted to be detachably connected to at least one of the dialysis machine and the extracorporeal circuit, the diafiltration module comprising:

a first conduit having a first end and an opposing second end, the first end for receiving a dialysate fluid from the dialysis machine and the second end for discharging the dialysate fluid to the dialyzer;

a second conduit in selective communication with the first conduit such that the second conduit selectively receives a diverted amount of the dialysate fluid from the first conduit, the second conduit communicating with at least one sterilizing filter for filtering the diverted amount of the dialysate fluid to produce a substitution fluid, wherein one end of the second conduit is configured to deliver the substitution fluid to the extracorporeal circuit;

a control unit responsive to a first detected characteristic of one of the dialysate fluid flowing within the first conduit and the diverted dialysate fluid flowing within the second conduit, the control unit being configured to prevent flow of substitution fluid to the extracorporeal circuit by controlling flow of the diverted dialysate fluid within the second conduit in the control module when at least the first detected characteristic meets a prescribed criteria, wherein the control unit is responsive to a second detected characteristic of blood within the extracorporeal circuit, the second detected characteristic being a flow rate of the blood, wherein the control unit is configured to prevent flow of substitution fluid to the extracorporeal circuit by controlling flow of the diverted dialysate fluid within the second conduit in the control module when at least the second detected characteristic meets a prescribed criteria, wherein the first detected characteristic is calculated using a temperature decay measurement of one of the dialysate fluid and the diverted dialysate fluid and the second detected characteristic is calculated using a temperature decay measurement of the blood and the diafiltration module further includes:

a first temperature sensing device for detecting the temperature of one of the dialysate fluid in the first conduit and the diverted dialysate fluid in the second conduit, the first temperature sensing device in communication with the control unit and inputting the detected temperature to the control unit;

a second temperature sensing device for detecting the temperature of blood in the extracorporeal circuit, the second temperature sensing device in communication with the control unit and inputting the detected temperature to the control unit; and wherein the control unit is configured to detect a decrease in flow rate of one of the dialysate fluid and the diverted dialysate fluid by monitoring the detected temperature inputted from the first temperature sensing device and a decrease in a blood flow rate within the extracorporeal circuit by monitoring the detected temperature inputted from the second temperature sensing device.

17. The diafiltration module according to claim 16, wherein the first temperature sensing device is disposed in one of (a) a location inside of the first conduit and (b) on an outer surface of the first conduit.

18. The diafiltration module according to claim 17, wherein the first temperature sensing device comprises one of a thermistor and thermocouple that is disposed inside of the first conduit.

19. The diafiltration module according to claim 16, wherein the second temperature sensing device is disposed in one of (a) a location inside of a conduit defining the extracorporeal circuit and (b) on an outer surface of the conduit defining the extracorporeal circuit.

20. The diafiltration module according to claim 15, wherein the temperature decay measurement is determined as one of (a) a change in temperature from a fixed set point and (b) a change in temperature per unit time.

21. The diafiltration module according to claim 17, wherein the first temperature sensing device comprises one of a thermistor and thermocouple that is disposed on the outer surface of the first conduit.

22. In a blood dialysis system including a dialysis machine and an extracorporeal circuit including a dialyzer, a diafiltration module that is an independent standalone unit relative to the dialysis machine and the extracorporeal circuit and is adapted to be detachably connected to at least one of the dialysis machine and the extracorporeal circuit, the diafiltration module comprising:

a first conduit having a first end and an opposing second end, the first end for receiving a dialysate fluid from the dialysis machine and the second end for discharging the dialysate fluid to the dialyzer;

a second conduit in selective communication with the first conduit such that the second conduit selectively receives a diverted amount of the dialysate fluid from the first conduit, the second conduit communicating with at least one sterilizing filter for filtering the diverted amount of the dialysate fluid to produce a substitution fluid, wherein one end of the second conduit is configured to deliver the substitution fluid to the extracorporeal circuit;

a control unit responsive to a first detected characteristic of one of the dialysate fluid flowing within the first conduit and the diverted dialysate fluid flowing within the second conduit, the control unit being configured to prevent flow of substitution fluid to the extracorporeal circuit by controlling flow of the diverted dialysate fluid within the second conduit in the control module when at least the first detected characteristic meets a prescribed criteria, wherein the control unit is responsive to a second detected characteristic of blood within the extracorporeal circuit, the second detected characteristic being a flow rate of the blood, wherein the control unit is configured to prevent flow of substitution fluid to the extracorporeal circuit by controlling flow of the diverted dialysate fluid within the second conduit in the control module when at least the second detected characteristic meets a prescribed criteria, wherein the control unit is configured to prevent flow of the substitution fluid to the extracorporeal circuit when at least one of the first and second detected characteristics meets a prescribed criteria, wherein the second detected characteristic is detected by a rotational speed measurement of a blood pump that is part of the dialysis machine and is disposed within the extracorporeal circuit and wherein the prescribed criteria comprises a minimum rotational speed such that once the detected rotational speed measurement falls below the minimum rotational speed, the control unit prevents flow of the substitution fluid.

23. The diafiltration module according to claim 22, further including:

a tachometer device that measures the rotational speed of the blood pump.

24. In a blood dialysis system including a dialysis machine and an extracorporeal circuit including a dialyzer, a diafiltration module that is an independent standalone unit relative to the dialysis machine and the extracorporeal circuit and is adapted to be detachably connected to at least one of the dialysis machine and the extracorporeal circuit, the diafiltration module comprising:

a first conduit having a first end and an opposing second end, the first end for receiving a dialysate fluid from the dialysis machine and the second end for discharging the dialysate fluid to the dialyzer;

a second conduit in selective communication with the first conduit such that the second conduit selectively receives a diverted amount of the dialysate fluid from the first conduit, the second conduit communicating with at least one sterilizing filter for filtering the diverted amount of the dialysate fluid to produce a substitution fluid, wherein one end of the second conduit is configured to deliver the substitution fluid to the extracorporeal circuit;

a control unit responsive to a first detected characteristic of one of the dialysate fluid flowing within the first conduit and the diverted dialysate fluid flowing within the second conduit, the control unit being configured to prevent flow of substitution fluid to the extracorporeal circuit by controlling flow of the diverted dialysate fluid within the second conduit in the control module when at least the first detected characteristic meets a prescribed criteria, wherein the control unit is responsive to a second detected characteristic of blood within the extracorporeal circuit, the second detected characteristic being a flow rate of the blood, wherein the control unit is configured to prevent flow of substitution fluid to the extracorporeal circuit by controlling flow of the diverted dialysate fluid within the second conduit in the control module when at least the second detected characteristic meets a prescribed criteria, wherein the control unit is configured to prevent flow of the substitution fluid to the extracorporeal circuit when at least one of the first and second detected characteristics meets a prescribed criteria, wherein the second detected characteristic is detected by monitoring a fluid level fluctuation of the blood within a drip chamber that is provided along the extracorporeal circuit and wherein the prescribed criteria is when the fluid level fluctuation is below an acceptable fluid level fluctuation value, thereby preventing the flow of substitution fluid to the extracorporeal circuit.

25. The diafiltration module according to claim 24, further including:
- a substitution fluid pump disposed within the second conduit for diverting the amount of the dialysate fluid from the first conduit to the second conduit, the substitution fluid pump being in communication with the control unit; and
- wherein the control unit detects whether a blood pump disposed within the extracorporeal circuit is operating within prescribed acceptable operating conditions by detecting the fluid level fluctuations in the drip chamber such that if the detected fluid level fluctuation is below an acceptable fluid level fluctuation value, the substitution fluid pump is turned to the OFF position.

26. In a blood dialysis system including a dialysis machine and an extracorporeal circuit including a dialyzer, a diafiltration module that is an independent standalone unit relative to the dialysis machine and the extracorporeal circuit and is adapted to be detachably connected to at least one of the dialysis machine and the extracorporeal circuit, the diafiltration module comprising:
- a first conduit having a first end and an opposing second end, the first end for receiving a dialysate fluid from the dialysis machine and the second end for discharging the dialysate fluid to the dialyzer;
- a second conduit in selective communication with the first conduit such that the second conduit selectively receives a diverted amount of the dialysate fluid from the first conduit, the second conduit communicating with at least one sterilizing filter for filtering the diverted amount of the dialysate fluid to produce a substitution fluid, wherein one end of the second conduit is configured to deliver the substitution fluid to the extracorporeal circuit;
- a control unit responsive to a first detected characteristic of one of the dialysate fluid flowing within the first conduit and the diverted dialysate fluid flowing within the second conduit, the control unit being configured to prevent flow of substitution fluid to the extracorporeal circuit by controlling flow of the diverted dialysate fluid within the second conduit in the control module when at least the first detected characteristic meets a prescribed criteria, wherein the first detected characteristic is detected by inductively monitoring a current applied to an inlet valve that is disposed within a feed conduit that carries the dialysate fluid from the dialysis machine to one end of the first conduit.

27. In a blood dialysis system including a dialysis machine and an extracorporeal circuit including a dialyzer, a diafiltration module that is an independent standalone unit relative to the dialysis machine and the extracorporeal circuit and is adapted to be detachably connected to at least one of the dialysis machine and the extracorporeal circuit, the diafiltration module comprising:
- a first conduit having a first end and an opposing second end, the first end for receiving a dialysate fluid from the dialysis machine and the second end for discharging the dialysate fluid to the dialyzer;
- a second conduit in selective communication with the first conduit such that the second conduit selectively receives a diverted amount of the dialysate fluid from the first conduit, the second conduit communicating with at least one sterilizing filter for filtering the diverted amount of the dialysate fluid to produce a substitution fluid, wherein one end of the second conduit is configured to deliver the substitution fluid to the extracorporeal circuit;
- a control unit responsive to a first detected characteristic of one of the dialysate fluid flowing within the first conduit and the diverted dialysate fluid flowing within the second conduit, the control unit being configured to prevent flow of substitution fluid to the extracorporeal circuit by controlling flow of the diverted dialysate fluid within the second conduit in the control module when at least the first detected characteristic meets a prescribed criteria, wherein the control unit is responsive to a second detected characteristic of blood within the extracorporeal circuit, the second detected characteristic being a flow rate of the blood, wherein the control unit is configured to prevent flow of substitution fluid to the extracorporeal circuit by controlling flow of the diverted dialysate fluid within the second conduit in the control module when at least the second detected characteristic meets a prescribed criteria, wherein the second detected characteristic is detected by inductively monitoring a current applied to a motor that drives a blood pump disposed within the extracorporeal circuit.

28. The diafiltration module according to claim 26, further including:
- a first inductive current clamp disposed around wires leading to the inlet valve, the first inductive current clamp in communication with the control unit, the control unit preventing flow of substitution fluid when the first inductive current clamp detects an absence of current.

29. The diafiltration module according to claim 27, further including:
- a second inductive current clamp disposed around wires leading to the blood pump, the second inductive current clamp in communication with the control unit which prevents the flow of substitution fluid when the second inductive current clamp detects an absence of current.

30. In a blood dialysis system including a dialysis machine and an extracorporeal circuit including a dialyzer, a dialfiltration module that is an independent standalone unit relative to the dialysis machine and the extracorporeal circuit and is adapted to be detachably connected to at least one of the dialysis machine and the extracorporeal circuit, the diafiltration module comprising:
- a first conduit having a first end and an opposing second end, the first end for receiving a dialysate fluid from the dialysis machine and the second end for discharging the dialysate fluid to the dialyzer;
- a second conduit in selective communication with the first conduit such that the second conduit selectively receives a diverted amount of the dialysate fluid from the first conduit, the second conduit communicating with at least one sterilizing filter for filtering the diverted amount of the dialysate fluid to produce a substitution fluid, wherein one end of the second conduit is configured to deliver the substitution fluid to the extracorporeal circuit;
- a control unit responsive to a first detected characteristic of one of the dialysate fluid flowing within the first conduit and the diverted dialysate fluid flowing within the second conduit, the control unit being configured to prevent flow of substitution fluid to the extracorporeal circuit by controlling flow of the diverted dialysate fluid within the second conduit in the control module when at least the first detected characteristic meets a prescribed criteria, wherein the control unit is responsive to a second detected characteristic of blood within the extracorporeal circuit, the second detected characteristic being a flow rate of the blood, wherein the control unit is configured to prevent flow of substitution fluid to the extracorporeal circuit by controlling flow of the diverted dialysate fluid within the second conduit in the control module when at least the second detected characteristic meets a prescribed criteria, wherein the second detected characteristic is detected by sensing vibrations generated by a blood pump that is disposed in the extracorporeal circuit.

31. The diafiltration module according to claim 30, wherein the vibrations are sensed mechanically or acoustically.

32. In a blood dialysis system including a dialysis machine that includes a source of dialysate fluid and an extracorporeal circuit, a method of preventing flow of substitution fluid to the extracorporeal circuit comprising the steps of:

providing a diafiltration module including a first conduit having a first end and a second end for carrying dialysate fluid and a second conduit in selective communication with the first conduit such that the second conduit selectively receives a diverted amount of the dialysate fluid, the diafiltration module further including at least one sterilizing filter in fluid communication with the second conduit for filtering the diverted dialysate fluid to produce the substitution fluid; fluidly connecting the first end of the first conduit to the dialysis machine so that the dialysate fluid flows from the source to the first conduit; fluidly connecting the second conduit to the extracorporeal circuit such that the substitution fluid is delivered and introduced into the extracorporeal circuit;

providing a control unit;

detecting a first characteristic of the dialysate fluid flowing within the first conduit and detecting a second characteristic of the blood flowing within the extracorporeal circuit; and inputting the detected first and second characteristics to the control unit, wherein the control unit is configured to prevent the flow and introduction of the substitution fluid into the extracorporeal circuit when at least the first characteristic meets a prescribed criteria wherein the first characteristic comprises a flow rate of the dialysate fluid and the second characteristic comprises a flow rate of the blood and the prescribed criteria comprises a situation where the dialysate flow rate falls below a predetermined flow rate.

33. The method of claim 32, further including the step of:

disposing a substitution fluid pump within the second conduit for diverting the amount of the dialysate fluid from the first conduit to the second conduit, wherein the control unit prevents the substitution fluid from being introduced into the extracorporeal circuit by controlling operation of the substitution fluid pump.

34. The method of claim 33, wherein detecting the first characteristic comprises the steps of:

disposing a pressure transducer within the second conduit for detecting a pressure of the dialysate fluid within the second conduit; and transmitting a control signal from the control unit to the substitution fluid pump to turn to an OFF position when the pressure transducer detects a pressure below a threshold pressure value.

35. The method of claim 33, wherein detecting the first characteristic comprises the steps of:

disposing a pressure transducer within the second conduit for detecting a pressure of the dialysate fluid within the second conduit; disposing a pinch valve within the second conduit for controlling the flow of the substitution fluid within the second conduit; and transmitting a control signal from the control unit to the pinch valve to position the pinch valve in response to the control unit receiving input from the substitution fluid pump and the pressure transducer.

36. The method of claim 35, further including the step of: disposing an optical sensor disposed within the second conduit for detecting transmittance of fluid contained in the second conduit; and positioning the pinch valve by transmitting a control signal to the pinch valve from the control unit in response to input received by the control unit from the optical sensor.

37. The method of claim 36, further including the step of: closing the pinch valve when the optical sensor detects blood in the second conduit.

38. The method of claim 33, further including the steps of:

disposing a flow switch within the first conduit for detecting a flow rate within the first conduit; and controlling the operation of the substitution fluid pump based on a position of the flow switch.

39. The method of claim 32, wherein detecting the first and second characteristics comprise the steps of:

performing a first temperature decay measurement of the dialysate fluid in the first conduit, the first temperature decay measurement being representative of a flow rate of the dialysate fluid; performing a second temperature decay measurement of the blood in the extracorporeal circuit, the second temperature decay measurement being representative of a flow rate of the blood; and wherein the control unit is configured to detect a decrease in the flow rate of the dialysate fluid by monitoring the first temperature decay measurement and a decrease in the flow rate of the blood by monitoring the second temperature decay measurement.

40. The method of claim 32, wherein the first detected characteristic is detected by inductively monitoring a current applied to an inlet valve of the dialysis machine that is disposed within a conduit that carries the dialysate fluid to the first conduit and wherein the second detected characteristic is detected by inductively monitoring a current applied to a motor that drives a blood pump disposed within the extracorporeal circuit.

41. The diafiltration module according to claim 1, further including a substitution fluid pump disposed within the second conduit upstream of the at least one sterilizing filter for diverting the amount of the dialysate fluid from the first conduit to the second conduit, the substitution fluid pump being in communication with the control unit.

* * * * *